United States Patent
Rao

(10) Patent No.: US 9,365,867 B2
(45) Date of Patent: Jun. 14, 2016

(54) PROTEIN AND NUCLEIC ACID DELIVERY VEHICLES, COMPONENTS AND MECHANISMS THEREOF

(71) Applicant: THE CATHOLIC UNIVERSITY OF AMERICA, Washington, DC (US)

(72) Inventor: Venigalla B. Rao, Silver Spring, MD (US)

(73) Assignee: The Catholic University of America, Washington, DC (US)

( * ) Notice: Subject to any disclaimer, the term of this patent is extended or adjusted under 35 U.S.C. 154(b) by 262 days.

(21) Appl. No.: 13/796,263

(22) Filed: Mar. 12, 2013

(65) Prior Publication Data

US 2013/0196416 A1 Aug. 1, 2013

Related U.S. Application Data

(62) Division of application No. 13/082,466, filed on Apr. 8, 2011, now Pat. No. 8,802,418.

(60) Provisional application No. 61/322,334, filed on Apr. 9, 2010.

(51) Int. Cl.

| | |
|---|---|
| C12N 7/00 | (2006.01) |
| C12N 15/86 | (2006.01) |
| A61K 31/7088 | (2006.01) |
| A61K 31/711 | (2006.01) |
| C12N 15/87 | (2006.01) |
| C12N 15/88 | (2006.01) |
| C07K 14/005 | (2006.01) |
| A61K 47/48 | (2006.01) |
| A61K 48/00 | (2006.01) |

(52) U.S. Cl.
CPC ............ *C12N 15/86* (2013.01); *A61K 31/7088* (2013.01); *A61K 31/711* (2013.01); *A61K 47/48776* (2013.01); *C07K 14/005* (2013.01); *C12N 7/00* (2013.01); *C12N 15/87* (2013.01); *C12N 15/88* (2013.01); *A61K 48/00* (2013.01); *C12N 2795/10042* (2013.01); *C12N 2795/10122* (2013.01); *C12N 2795/10142* (2013.01); *C12N 2795/10152* (2013.01)

(58) Field of Classification Search
None
See application file for complete search history.

(56) References Cited

U.S. PATENT DOCUMENTS

| | | |
|---|---|---|
| 2005/0226892 A1 | 10/2005 | Rao |
| 2008/0274533 A1 | 11/2008 | Alving et al. |
| 2009/0113562 A1 | 4/2009 | Sokoloff et al. |
| 2010/0304445 A1 | 12/2010 | Szybalski et al. |

FOREIGN PATENT DOCUMENTS

| | | |
|---|---|---|
| CN | 1972710 A | 5/2007 |
| JP | 2007-514762 | 6/2007 |
| WO | 96/21007 | 7/1996 |
| WO | 2005058006 A2 | 6/2005 |
| WO | 2007/015704 A2 | 2/2007 |

OTHER PUBLICATIONS

Jiang et al., "Display of a PorA Peptide from Neisseria meningitidis on the Bacteriophage T4 Capsid surface," Infection and Immunity 65:4770-77 (1997).
Clark JR and March JB, "Bacteriophage-mediated nucleic acid immunization," FEMS Immunology and Medical Microbiology, 40, 21-26 (2004).
March et al., "Genetic immunisation against hepatitis B using whole bacteriophage lambda particles," Vaccine, 22, 1666-71 (2004).
Kondabagil et al., "The DNA translocating ATPase of bacteriophage T4 packaging motor," J. Mol. Biol., 363: 786-99 (2006).
Lata et al., "Maturation Dynamics of a Viral Capsid: Visualization of Transitional Intermediate States," Cell. 100(2), 253-263 (2000).
Gertsman et al., "An unexpected twist in viral capsid maturation," Nature, 458, 646-50 (2009).
Rao et al., "Structure and assembly of bacteriophage T4 head," Virol. J. 7:356 (2010).
Rossmann et al., "The bacteriophage T4 DNA injection machine," Curr. Opin. Struct. Biol. 14(2):171-80 (2004).
Kostyuchenko et al., "Three-dimensional structure of bacteriophage T4 baseplate," Nat. Struct. Biol. 10(9):688-93 (2003).
Tao et al., "Assembly of a tailed bacterial virus and its genome release studied in three dimensions," Cell 95(3): 431-37(1998).
PloS Biol. 9(2):310000592 (2011).
Rao et al., "DNA Packaging in Bacteriophage T4," Madame Curie Bioscience Database, Landes Bioscience, (2000).
Sun et al., "The structure of the phage T4 DNA packaging motor suggests a mechanism dependent on electrostatic forces," Cell 135(7):1251-62 (2008).
Hendrix, "Evolution: the long evolutionary reach of viruses," Curr. Biol. 9: R914-R917 (1999).
Smith et al., "The bacteriophage straight phi29 portal motor can package DNA against a large internal force," Nature 413: 748-52 (2001).
Lander et al., "The structure of an infectious P22 virion shows the signal for headful DNA packaging," Science 312: 1791-95 (2006).

(Continued)

*Primary Examiner* — Michele K Joike
(74) *Attorney, Agent, or Firm* — Alchemy-Partners, PC

(57) ABSTRACT

Complex viruses are assembled from simple protein subunits by sequential and irreversible assembly. During genome packaging in bacteriophages, a powerful molecular motor assembles at the special portal vertex of an empty prohead to initiate packaging. An aspect of the invention relates to the phage T4 packaging machine being highly promiscuous, translocating DNA into finished phage heads as well as into proheads. Single motors can force exogenous DNA into phage heads at the same rate as into proheads and phage heads undergo repeated initiations, packaging multiple DNA molecules into the same head. This shows that the phage DNA packaging machine has unusual conformational plasticity, powering DNA into an apparently passive capsid receptacle, including the highly stable virus shell, until it is full. These features allow for the design of a novel class of nanocapsid delivery vehicles.

24 Claims, 15 Drawing Sheets

(56) References Cited

OTHER PUBLICATIONS

Casjens, "Control mechanisms in dsDNA bacteriophage assembly," The Bacteriophages, vol. 1, Calendar R, editor, New York: Plenum Press, 15-91 (1998).

Black et al., "Morphogenesis of the T4 head," Molecular biology of bacteriophage T4, Karam, editor, Washington, D.C.: American Society for Microbiology, 218-58 (1994).

Mettenleiter et al., "Herpesvirus assembly: an update," Virus Res. 143: 222-234 (2009).

Simpson et al., "Structure of the bacteriophage phi29 DNA packaging motor," Nature 408: 745-750 (2000).

Lebedev et al. "Structural framework for DNA translocation via the viral portal protein," EMBO J. 26: 1984-94 (2007)

Rao et al., "The bacteriophage DNA packaging motor," Annu. Rev. Genet. 42: 647-81 (2008).

Alam et al., "The headful packaging nuclease of bacteriophage T4," Mol. Microbiol. 69: 1180-90 (2008).

Rao, "A virus DNA gate: zipping and unzipping the packed viral genome," Proc. Natl. Acad. Sci., 106: 8403-04 (2009).

Zheng et al., "A conformational switch in bacteriophage p22 portal protein primes genome injection," Mol. Cell. 29: 376-83 (2008).

Bode et al., "The arrangement of DNA in lambda phage heads. I. Biological consequences of micrococcal nuclease attack on a portion of the chromosome exposed in tailless heads," J. Mol. Biol. 62: 493-502 (1971).

Lhuillier et al., "Structure of bacteriophage SPP1 head-to-tail connection reveals mechanism for viral DNA gating," Proc. Natl. Acad. Sci. 106: 8507-12 (2009).

Edgar et al., "Morphogenesis of bacteriophage T4 in extracts of mutant-infected cells," Proc. Natl. Acad. Sci. 55: 498-505 (1966).

Rao et al., "Cloning, overexpression and purification of the terminase proteins gp16 and gp17 of bacteriophage T4. Construction of a defined in-vitro DNA packaging system using purified terminase proteins," J. Mol. Biol. 200: 475-88 (1988).

Leffers et al., "Biochemical characterization of an ATPase activity associated with the large packaging subunit gp17 from bacteriophage T4," J. Biol. Chem. 275: 37127-136 (2000).

Rentas et al.,. "Defining the bacteriophage T4 DNA packaging machine: evidence for a C-terminal DNA cleavage domain in the large terminase/packaging protein gp17," J. Mol. Biol. 334: 37-52 (2003).

Baumann et al., "Isolation and characterization of T4 bacteriophage gp17 terminase, a large subunit multimer with enhanced ATPase activity," J. Biol. Chem. 278: 4618-27 (2003).

Sun et al., "The structure of the phage T4 DNA packaging motor suggests a mechanism dependent on electrostatic forces," Cell 135: 1251-1262 (2008).

van Duijn, "Current limitations in native mass spectrometry based structural biology," J. Am. Soc. Mass. Spectrom. 21: 971-78 (2010).

Al-Zahrani et al., "The small terminase, gp16, of bacteriophage T4 is a regulator of the DNA packaging motor," J. Biol Chem 284: 24490-500 (2009).

Wood, "Bacteriophage T4 morphogenesis as a model for assembly of subcellular structure," Q. Rev Biol. 55: 353-67 (1980).

King, "Assembly of the tail of bacteriophage T4," J. Mol. Biol. 32: 231-62 (1968).

Kikuchi et al., "Genetic control of bacteriophage T4 baseplate morphogenesis. I. Sequential assembly of the major precursor, in vivo and in vitro," J. Mol. Biol. 99: 645-72 (1975).

Ray et al., "Portal control of viral prohead expansion and DNA packaging," Virology 391: 44-50 (1999).

Carrascosa, "Head maturation pathway of bacteriophages T4 and T2. IV. In vitro transformation of T4 head-related particles produced by mutants in gene 17 to capsid-like structures," J. Virol. 26: 420-28 (1978).

Orlova et al., "Structure of the 13-fold symmetric portal protein of bacteriophage SPP1," Nat. Struct. Biol. 6: 842-846 (1999).

Casjens et al., "Bacteriophage P22 portal protein is part of the gauge that regulates packing density of intravirion DNA," J. Mol. Biol. 224: 1055-74 (1992).

Newcomb et al., "Polarized DNA ejection from the herpesvirus capsid," J. Mol. Biol. 392: 885-94 (2009).

Li et al., "Bacteriophage T4 capsid: a unique platform for efficient surface assembly of macromolecular complexes," J. Mol. Biol. 363: 577-88 (2006).

Archer et al., Sensors, 9,6298-311 (2009).

Li et al., "Assembly of the small outer capsid protein, Soc, on Bacteriophage T4: A novel system for high density display of multiple large anthrax toxins and foreign proteins on phage capsid," J. Mol. Biol. 370, 1006-1019 2007.

Wu et al., "Bacteriophage T4 nanoparticle capsid surface SOC and HOC bipartite display with enhanced classical swine fever virus immunogenicity: A powerful immunological approach," J. Virol. Meth. 139,50-60 (2007).

Mayhew et al., "Therapeutic applications of liposomes," Liposomes, Ostro, editor, Marcel Dekker: New York, 289-341 (1983).

Andre et al., "Increased immune response elicited by DNA vaccination with a synthetic gp120 sequence with optimized codon usage," J. Virol. 72:1497-1503 (1998).

Karlin et al., "Methods for assessing the statistical significance of molecular sequence features by using general scoring schemes" Proc. Natl. Acad. Sci. 87: 2264-68 (1990).

Karlin et al., "Applications and statistics for multiple high-scoring segments in molecular sequences," Proc. Natl. Acad. Sci. 90: 5873-77 (1993).

Myers et al., "Optimal alignments in linear space," CABIOS 4: 11-17 (1988).

Pearson et al., "Improved tools for biological sequence comparison," Proc. Natl. Acad. Sci. 85: 2444-48 (1988).

Altschul et al., "Local alignment statistics," Methods in Enzymology, Doolittle ed., 266: 460-80 (1996).

Altschul et al., J. Mol. Biol., 215: 403-410 (1990); Gish et al., Nature Genetics 3: 266-272 (1993).

Leiman et al., "Structure and morphogenesis of bacteriophage T4," Cell. Mol. Life Sci. 60: 2356-70 (2003).

Rao et al., "DNA packaging of bacteriophage T4 proheads in vitro. Evidence that prohead expansion is not coupled to DNA packaging," J. Mol. Biol. 185: 565-578 (1985).

Black et al., "Mechanistic coupling of bacteriophage T4 DNA packaging to components of the replication-dependent late transcription machinery," J. Biol. Chem. 281: 25635-25643 (2006).

Fokine et al., "Molecular architecture of the prolate head of bacteriophage T4," Proc Natl. Acad. Sci. 101: 6003-08 (2004).

Steven et al., "Conformational changes of a viral capsid protein : Thermodynamic rationale for proteolytic regulation of bacteriophage T4 capsid expansion, co-operativity, and super-stabilization by soc binding," J. Mol. Biol. 228: 870-84 (1992).

Bustamante et al., "High resolution dual trap optical tweezers with differential detection," Single-molecule techniques: a laboratory manual, Selvin et al., editors, Woodbury, NY: Cold Spring Harbor Laboratory Press. 297-324 (2007).

Chemla et al., "Mechanism of force generation of a viral DNA packaging motor," Cell 122: 683-692 (2005).

Roy et al., "A practical guide to single-molecule FRET," Nat. Methods 5: 507-16 (2008).

Rasnik et al., "Branch migration enzyme as a Brownian ratchet," EMBO J. 27: 1727-35 (2008).

Extended European Search Report issued in corresponding European Application No. 11765160.4 on Sep. 12, 2013 (14 pages).

Xiang, et al., "Crystal and cryoEM structural studies of a cell wall degrading enzyme in the bacteriophage Φ29 tail", XP-002712068, Department of Biological Sciences, Purdue University, West Lafayetts, IN 47907 et al.; Apr. 28, 2008 (6 pages).

Zanghi et al., "A tractable method for simultaneous modifications to the head and tail of bacteriophage lambda and its application to enhancing phage-mediated gene delivery", Mar. 28, 2007, Nucleic Acids Research, 2007, vol. 35, No. 8 (8 pages).

Atz et al., "Alanine Scanning and Fe-BABE Probing of the Bacteriophage Φ29 Prohead RNA-Connector Interaction", Science Direct, J. Mol. Biol. (2007) 369, 239-248.

Cai et al., "The effect of N- or C-terminal alterations of the connector of bacteriophage phi29 DNA packaging motor on procapsid assem-

(56) References Cited

OTHER PUBLICATIONS bly, pRNA binding, and DNA packaging", ScienceDirect, Nanomedicine: Nanotechnology, Biology, and Medicine 4 (2008) 8-18 (12 pages).
Cohen et al., "Shared Catalysis in Virus Entry and Bacterial Cell Wall Depolymerization", ScienceDirect, J. Mol. Biol. (2009) 387, 607-618 (12 pages).
Office Action received in European Patent No. 13 194 914.1; mailed Jan. 20, 2015.
Maruyama et al., "Afoo: A λ phage vector for the expression of foreign proteins", Proc. Natl. Acad. Sci. USA; vol. 91; pp. 8273-8277 (1994).
Zanghi et al., "A tractable method for simultaneous modifications to the head and tail of bacteriophage lambda and its application to enhancing phage-mediated gene delivery", Nucleic Acids Research; vol. 25; No. 8; e59; pp. 1-8 (2007).
Office Action received in Chinese Application No. 201400053507, mailed Feb. 27, 2015, and English language translation thereof.
Rao, et al., "The N-terminal ATPase Site in the Large Terminase Protein gp17 is Critically Required for DNA Packaging in Bacteriophage T4", J. Mol. Biol. 314; pp. 401-411 (2001).
Takeda et al., "Mapping of functional sites on the primary structure of the tail lysozyme of bacteriophage T4 by mutational analysis", Biochimica et Biophysica Acta 1384; pp. 243-252 (1998).
Extended European Search Report issued in corresponding European Application No. 13194914.1 on Jan. 7, 2014 (7 pages).
Maruyama I N et al: "Lambda Foo: A Lambda Phage Vector for the Expression of Foreign Proteins", Proceedings of the National Academy of Sciences, National Academy of Sciences, US, vol. 91, No. 17, Aug. 1, 1994, pp. 8273-8277.
Rao et al.,"The N-terminal ATPase Site in the Large Terminase Protein gp17 is Critically Required for DNA Packaging in Bacteriophage T4", *J. Mol. Biol.*, vol. 314, pp. 401-411 (2001).
Takeda et al., "Mapping of functional sites on the primary structure of the tail lysozyme of bacteriophage T4 by mutational analysis", *Biochimica et Biophysica Acta*, vol. 1384, pp. 243-252 (1998).
Lin et al., "Analysis of Capsid Portal Protein and Terminase Functional Domains: Interaction Sites Required for DNA Packaging in Bacteriophage T4", *J. Mol. Biol.*, vol. 289, pp. 249-260, (1999).
International Search Report and Written Opinion dated Jan. 13, 2012 received in PCT/IB2011/051533.
Cai et al., "The effect of N- or C-terminal alterations of the connector bacteriophage phi29 DNA packaging motor on procapsid assembly, pRNA binding, and DNA packaging", Nanomedicine: Nanotechnology, Biology, and Medicine, vol. 4, pp. 8-18 (2008).
Cohen et al, "Shared Catalysis in Virus Entry and Bacterial Cell Wall Depolymerization", J. Mol. Biol., vol. 387; pp. 607-618 (2009).
Xlang et al., "Crystal and cryoEM structural studies of a cell wall degrading enzyme in bacteriophage o29 tail", PNAS, vol. 105, No. 28, pp. 9552-9557 (2008).
Zanghi et al., "A tractable method for simultaneous modifications to the head and tail of bacteriophage lambda and its application to enhancing phage-mediated gene delivery", Nucleic Acids Research, vol. 35, No. 8 (2007).
European Office Action received in corresponding European Application No. 11765160.4, dated Sep. 16, 2014.
Office Action dated Jun. 6, 2015 received in European Patent Application No. 13194914.1.
Office Action received in Japanese Application No. 2013-503215 dated Apr. 21, 2015.
Translation of Office Action received in Japanese Application No. 2013-503215 dated Apr. 21, 2015.
Zhang et al. "A Promiscuous DNA Packaging Machine from Bacteriophage T4", PLOS Biology, vol. 9, No. 2, #e1000592 (2011).
Atz et al., "Alanine Scanning and Fe-BABE Probing of the Bacteriophage o29 Prohead RNA-Connector Interaction", J. Mol. Biol., vol. 369, pp. 239-248 (2007).
Cai et al., "The effect of N- or C-terminal alterations of the connector of bacteriophage phi29 DNA packaging motor on procapsid assembly, pRNA binding, and DNA packaging", Nanomedicine: Nanotechnology, Biology, and Medicine, vol. 4, pp. 8-18 (2008).
Lee et al., "In Vitro Assembly of Infections Virions of Double-Stranded DNA Phage o29 from Cloned Gene Products and Synthetic Nucleic Acids", Journal of Virology, vol. 69, No. 8, pp. 5018-5023 (1995).
Cohen et al., "Shared Catalysis in Virus Entry and Bacterial Cell Wall Depolymerization", J. Mol. Biol., vol. 387, pp. 607-618 (2009).
Xiang et al., "Crystal and cryoEM structural studies of a cell wall degrading enzyme in the bacteriophage 029 tail," PNAS, vol. 105, no. 28, pp. 9552-9557 (2008).
Zanghi et al., "A tractable method for simultaneous modifications to the head and tail of bacteriophage lambda and its application to enhancing phage-mediated gene delivery", Nucleic Acids Research, vol. 35, No. 8, #e59 (2007).
Johnson III et al., "Isolation and Characterization of Nonsense Mutations in Gene 10 of Bacteriophage o6", Journal of Virology, vol. 68, No. 4, pp. 2331-2338 (1994).
Kemp et al., "Changes in bacteriophage T7 virion structure at the initiation of infection", Virology, vol. 340, pp. 307-317 (2005).
Official Action received in European Application No. 13194914.1 mailed Feb. 2, 2016.
Office Action dated Aug. 14, 2015 received in Chinese Patent Application No. 201410005350.7.
Ionel et al., Molecular Rearrangements Involved in the Capsid Shell Maturation of Bacteriophage T7, J. Biol. Chem., 286(1), pp. 234-242 (2011).
Office Action received in U.S. Appl. No. 14/322,097 to Venigalla B. Rao, mailed Jan. 28, 2016.

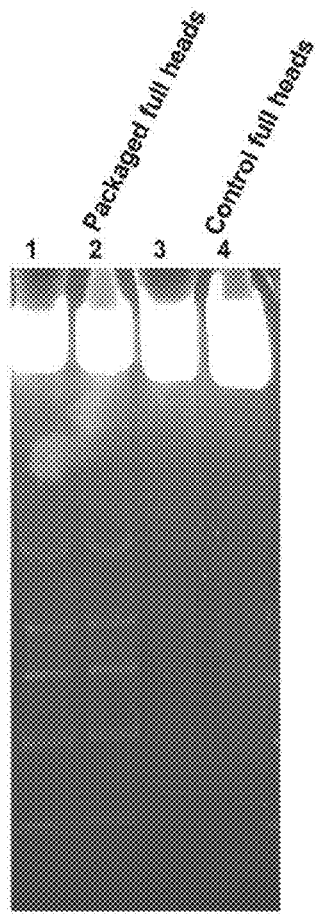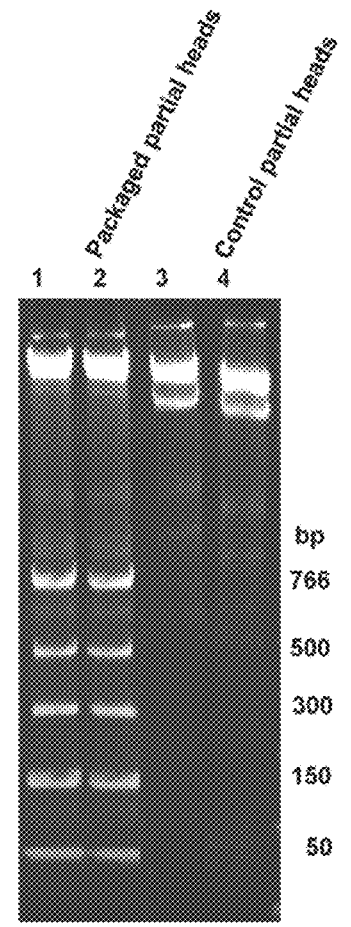
*FIG. 11*                              *FIG. 12*

PROTEIN AND NUCLEIC ACID DELIVERY VEHICLES, COMPONENTS AND MECHANISMS THEREOF

CROSS-REFERENCE TO RELATED APPLICATIONS

This application is a divisional application of U.S. patent application Ser. No. 13/082,466, filed Apr. 8, 2011, which claims benefit of priority to U.S. Provisional Patent Application No. 61/322,334 entitled "A Promiscuous DNA Packaging Machine from Bacteriophage T4" filed Apr. 9, 2010, the entire contents and disclosures of which are incorporated hereby reference.

GOVERNMENT INTEREST STATEMENT

The United States Government has rights in this invention pursuant to funding obtained from the National Institutes of Health (NIH) grant NIBIB 1R21 EB009869-01 and National Science Foundation grant MCB-0923873.

BACKGROUND

1. Field of the Invention

The present invention relates generally to protein and nucleic acid delivery components, compositions, mechanisms and methods of delivery thereof.

2. Related Art

The packaging competency of a matured capsid shell has not been discovered. There is still much to be desired for improved vehicles of gene therapy, especially for platforms that can deliver both nucleic acids and proteins. Outstanding issues relate to inefficiency of gene packaging, low amounts of genetic material being delivered, poor targeting and lack of tissue specificity. Other methods being employed for delivery of nucleic acids and proteins have a number of limitations: for example, the injection of naked DNA has very low expression; electroporation has a high rate of cell death associated with it; many viral vectors can only carry a small amount of nucleic acid for delivery; and there may be dose-related toxicity associated with cationic liposomal delivery. There is a need for a platform to be developed that addresses these issues.

SUMMARY

According one broad aspect, the present invention provides a method comprising the following steps: (a) attaching a packaging motor to a carrier and (b) transferring an exogenous material into an inner compartment of the carrier to thereby form a packaging machine.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 11 is an image of a gel in which full head bands from the gradient were treated with proteinase K and electrophoresed on a polyacrylamide gel.

FIG. 12 is an image of a gel in which partial head bands from the gradient were treated with proteinase K and electrophoresed on a polyacrylamide gel.

DETAILED DESCRIPTION OF THE PREFERRED EMBODIMENTS

Terminology

Figure 1:
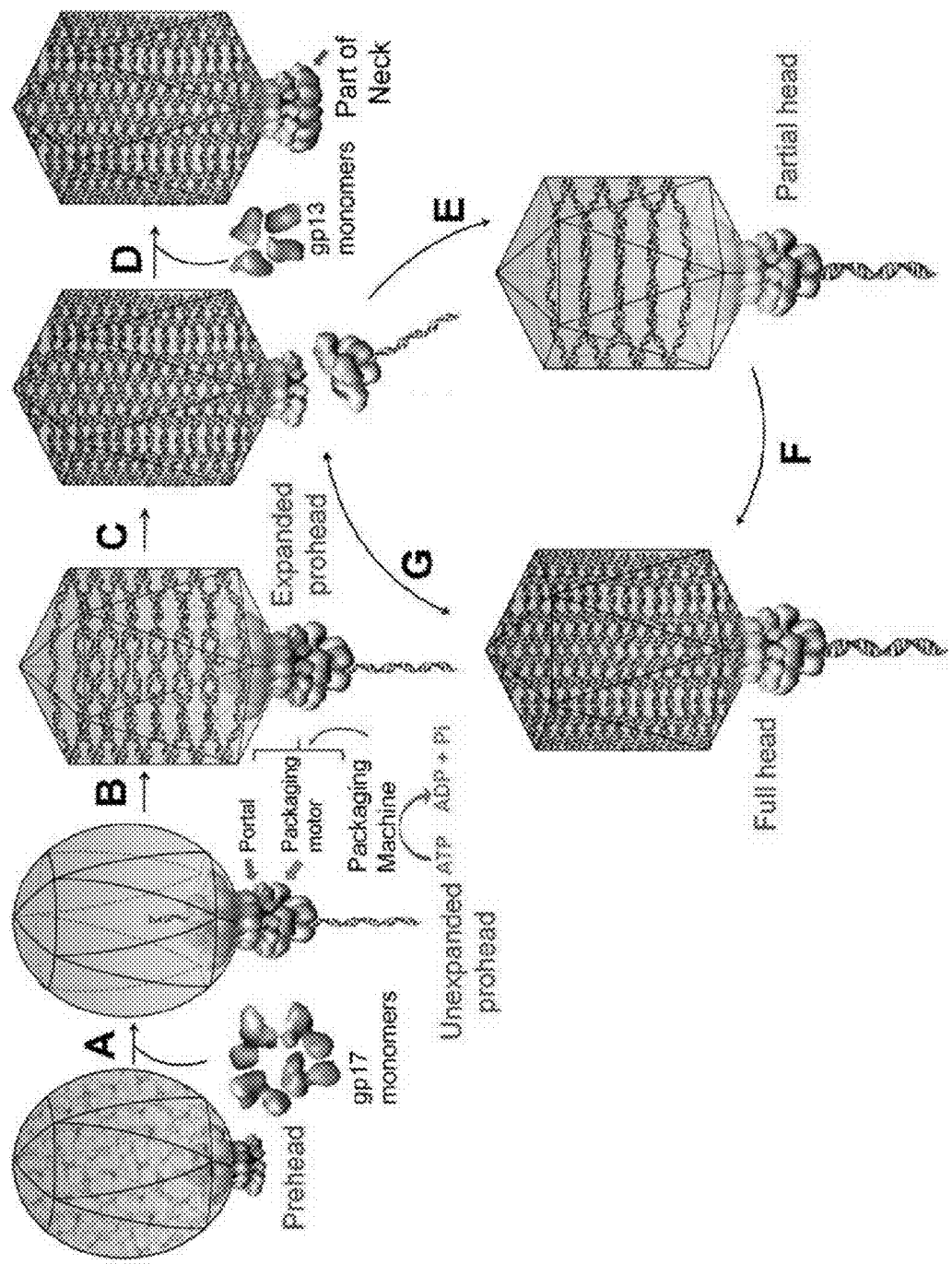
FIG. 1 is a schematic illustration showing DNA packaging by sequential assembly and promiscuous assembly.

Where the meaning of terms departs from the commonly used meaning of the term, applicant intends to utilize the terminology provided below, unless specifically indicated.

For purposes of the present invention, the term "bacteriophage component" refers to bacteriophages and bacteriophage derivatives, including bacteriophages and bacteriophage derivatives having antigens, fusion proteins and other types of molecules attached thereto. For example, the term "T4 bacteriophage component" refers to T4 bacteriophages and T4 bacteriophage derivatives.

For purposes of the present invention, the term "bacteriophage derivative" refers to any structure including at least part of the protein coat of a bacteriophage. An example of a bacteriophage derivative is where foreign DNA is packaged into a customized bacteriophage's genome is described, for example, in Jiang et al., "Display of a PorA Peptide form *Neisseria meningitidis* on the Bacteriophage T4 Capsid surface," *Infection and Immunity* 65:4770-77 (1997), Clark J R and March J B, "Bacteriophage-mediated nucleic acid immunization," *FEMS Immunology and Medical Microbiology*, 40, 21-26 (2004) and March et al., "Genetic immunisation against hepatitis B using whole bacteriophage lambda particles," *Vaccine,* 22, 1666-71 (2004), the entire contents and disclosures of which are incorporated herein by reference. Another example of a bacteriophage derivative is a bacteriophage capsid. Another example of a bacteriophage derivative is a bacteriophage tail. In one embodiment of the present invention, foreign DNA may be loaded into empty T4 capsids using the methods described in Kondabagil et al., "The DNA translocating ATPase Of bacteriophage T4 packaging motor," *J. Mol. Biol.,* 363: 786-99 (2006), the entire contents and disclosures of which are incorporated herein by reference.

For purposes of the present invention, the term "bind," the term "binding" and the term "bound" refers to any type of chemical or physical binding, which includes but is not limited to covalent binding, hydrogen binding, electrostatic binding, biological tethers, transmembrane attachment, cell surface attachment and expression.

For purposes of the present invention, the term "biological sample" and the term "biological specimen" refers to either a part or the whole of a human, animal, microbe or plant in vitro or in vivo. The term includes but is not limited to material of human, animal, microbe or plant origin such as human, animal, microbial or plant tissue sections, cell or tissue cultures, suspension of human, animal, microbial or plant cells or isolated parts thereof, human or animal biopsies, blood samples, cell-containing fluids and secretion.

For purposes of the present invention, the term "capsid coat protein" refers to the proteins that come together in many copies to form a capsid shell of a virus. For example, the T4 bacteriophage capsid is constituted by 930 copies of a single major capsid protein, gp23 (46 kDa). The capsid also consists of 55 copies of another minor capsid protein located at eleven of the 12 vertices (one pentamer at each vertex) of the minor capsid protein gp24 (42 kDa). Structural studies have established that two additional proteins, namely Hoc (Highly antigenic outer capsid protein, 40 kDa) and Soc (Small outer capsid protein, 9 kDa), are added onto the capsid after completion of capsid assembly Hoc is present up to 155 copies per capsid particle, whereas Soc is present up to 810 copies per capsid particle. These proteins may be considered nonessential. Mutations in either of the genes, or in both the genes, do not affect phage production, phage viability, phage infectivity, or phage stability under normal experimental conditions. However, Hoc and Soc provide additional stability to the capsid under extreme environmental conditions. Capsid coat proteins of the T4 bacteriophage and other phages are described, for example, in U.S. Patent Application. No. 2005/0226892 to Rao, entitled, "Methods and compositions comprising bacteriophage nanoparticles," published Oct. 13, 2005, the entire contents and disclosure of which in incorporated herein by reference.

For purposes of the present invention, the term "capsid" and the term "capsid shell" refers to the protein shell of a virus comprising several structural subunits of proteins. The capsid encloses the nucleic acid core of the virus. The terms "prehead," "prohead" or "procapsid," "partial head" or "partially filled head," "full head" and "phage head" in singular or plural form, refer to different stages of maturity of the viral capsid shell. "Prehead" refers to a capsid shell of precise dimensions or an isometric capsid that is initially assembled, often with a single type of protein subunit polymerizing around a protein scaffold. When the protein scaffolding is removed, creating an empty space inside the capsid shell, the structure is referred to as a prohead or a procapsid. Partial head, full head and phage head all refer to capsids that reach a stage of maturation that makes them larger, stabler particles associated with DNA. The term "partial head" refers to a mature capsid shell that either has only a portion of DNA packaged into it or it may refer to a mature capsid shell that was once packed full with DNA and then the DNA releases from the shell to leave only a small portion of DNA behind. The term "full head" refers to a mature capsid shell that is fully packed with DNA. Full heads can pack up to 105% of the bacteriophage genome. This is about 165-170 kb for T4 bacteriophages. Similarly, capsids of other viruses can also be packaged to accommodate more than their genomic volume. The capsid may or may not be enveloped. The maturation process of capsids in bacteriophages like HK97 is described, for example, in Lata et al., "Maturation Dynamics of a Viral Capsid: Visualization of Transitional Intermediate States," *Cell.* 100(2), 253-263 (2000), as well as in Gertsman et al., "An unexpected twist in viral capsid maturation," *Nature,* 458, 646-50 (2009), and in bacteriophages like T4 in Rao et al., "Structure and assembly of bacteriophage T4 head," *Virol. J.* 7:356 (2010), by reference.

For purposes of the present invention, the term "carrier" refers to any support structure that brings about the transfer of a component of genetic material or a protein. Genetic material includes but is not limited to DNA, RNA or fragments thereof and proteins or polypeptides comprise amino acids and include but are not limited to antigens, antibodies, ligands, receptors or fragments thereof. Carriers include but are not limited to vectors such as viruses (examples include but are not limited to retroviruses, adenoviruses, adeno-associated viruses, pseudotyped viruses, replication competent viruses, herpes simplex virus), virus capsids, liposomes or liposomal vesicles, lipoplexes, polyplexes, dendrimers, macrophages, artificial chromosomes, nanoparticles, polymers and also hybrid particles, examples of which include virosomes. Carriers may have multiple surfaces and compartments for attachment and storage of components. These include but are not limited to outer surfaces and inner compartments.

For purposes of the present invention, the term "epitope" refers to the smallest part of an antigen moiety recognizable by the combining site of an immunoglobulin.

For purposes of the present invention, the term "exogenous material" refers to material that originates outside the organism of concern or material that may be isolated from a organism, manipulated to any extent externally and then reintroduced into its natural environment or the environment from which it was isolated. Exogenous material includes but is not limited to nucleic acids, proteins, polymeric compounds, particulate matter and artificially synthesized material. For example, "exogenous nucleic acid" refers to any nucleic acid, DNA or RNA or fragments thereof, either single or double stranded, that originates outside of the organism of concern or was isolated from the organism, modified and reintroduced into the organism. Exogenous DNA present in a host cell may be derived from a source organism, cloned into a vector and then introduced into a host cell.

For purposes of the present invention, the term "immune response" refers to a specific response of the immune system of an animal to antigen or immunogen. Immune response may include the production of antibodies and cellular immunity.

For purposes of the present invention, the term "immunity" refers to a state of resistance of a subject animal including a human to an infecting organism or substance. It will be understood that an infecting organism or substance is defined broadly and includes parasites, toxic substances, cancer cells and other cells as well as bacteria and viruses. A "Therapeutically Effective Immunization Course" (see below for definition) will produce the immune response.

For purposes of the present invention, the term "immunization conditions" refers to factors that affect an immune response including the amount and kind of immunogen or adjuvant delivered to a subject animal including a human, method of delivery, number of inoculations, interval of inoculations, the type of subject animal and its condition. "Vaccine" refers to pharmaceutical formulations able to induce immunity.

For purposes of the present invention, the term "immunization dose" refers to the amount of antigen or immunogen needed to precipitate an immune response. This amount will vary with the presence and effectiveness of various adjuvants. This amount will vary with the animal and the antigen, immunogen and/or adjuvant but will generally be between about 0.1 µg/ml or less and about 100 µg per inoculation. The immunization dose is easily determined by methods well known to those skilled in the art, such as by conducting statistically valid host animal immunization and challenge studies as described: for example, Manual of Clinical Immunology, H. R. Rose and H. Friedman, American Society for Microbiology, Washington, D.C. (1980), tithe entire contents and disclosures of which are incorporated herein by reference. In some instances, several immunization doses including booster doses may administered to provide immunity, and, For purposes of the present invention such a course of treatment is collectively referred to as "Therapeutically Effective Immunization Course".

For purposes of the present invention, the term "immunogen" and the term "immunogenic" refers to a substance or material (including antigens) that is able to induce an immune response alone or in conjunction with an adjuvant. Both natural and synthetic substances may be immunogens. An immunogen is generally a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozoal fractions. It will be understood that "immunogen" or a composition that is "immunogenic" includes substances (e.g., small peptides) that do not generate an immune response (or generate only a therapeutically ineffective immune response) unless associated with an adjuvant. For purposes of the present invention, such immunogens are referred to as "adjuvant-obligatory" immunogens.

For purposes of the present invention, the term "immunogenic amount" is an amount of an antigen preparation of interest or amount of a biological toxin that elicits a clinically detectable protective response in an animal.

For purposes of the present invention, the term "liposome" and the term "liposomal vesicle" refers to a vesicle composed of a bilayer membrane, such as a bilayer membrane composed of a phospholipid and a cholesterol bilayer. Liposomes may also contain other steroid components such as polyethylene glycol derivatives of cholesterol (PEG-cholesterols), coprostanol, cholestanol, or cholestane, and combinations of PC and cholesterol. Liposomes may also contain glycolipids. Aspects of liposomes are further described in U.S. Patent Application No. 2008/0274533 to Alving et al, entitled "T4 Bacteriophage Bound to a Substrate," published Nov. 6, 2008, the entire contents and disclosures of which are incorporated herein by reference.

For purposes of the present invention, the term "neck protein" and the term "tail protein" refers to proteins that are involved in the assembly of any part of the necks or tails of a virus particle, in particular bacteriophages. Tailed bacteriophages belong to the order Caudovirales and include three families: The Siphoviridae have long flexible tails and constitute the majority of the tailed viruses. Myoviridae have long rigid tails and are fully characterized by the tail sheath that contracts upon phage attachment to bacterial host. The smallest family of tailed viruses are podoviruses (phage with short, leg-like tails). For example, in T4 bacteriophage gp10 associates with gp11 to forms the tail pins of the baseplate. Tail pin assembly is the first step of tail assembly. The tail of bacteriophage T4 consists of a contractile sheath surrounding a rigid tube and terminating in a multiprotein baseplate, to which the long and short tail fibers of the phage are attached. Once the heads are packaged with DNA, the proteins gp13, gp14 and gp15 assemble into a neck that seals of the packaged heads, with gp13 protein directly interacting with the portal protein gp20 following DNA packaging and gp14 and gp15 then assembling on the gp13 platform. Neck and tail proteins in T4 bacteriophage may include but are not limited to proteins gp6, gp25, gp53, gp8, gp10, gp11, gp7, gp29, gp27, gp5, gp28, gp12, gp9, gp48, gp54, gp3, gp18, gp19, gp13, gp14, gp15 and gp63. Aspects of the neck and tail assembly proteins in T4 bacteriophage and other viruses are described further, for example, in Rossmann et al., "The bacteriophage T4 DNA injection machine," *Curr. Opin. Struct. Biol.* 14(2):171-80 (2004), Kostyuchenko et al., "Three-dimensional structure of bacteriophage T4 baseplate," *Nat. Struct. Biol.* 10(9):688-93 (2003), Tao et al., "Assembly of a tailed bacterial virus and its genome release studied in three dimensions," *Cell* 95(3): 431-37 (1998), the entire contents and disclosures of which are incorporated herein by reference.

For purposes of the present invention, the term "non-naturally occurring" or "isolated" refers to the component of interest being at least substantially free from at least one other component with which it is naturally associated in nature and as found in nature.

For purposes of the present invention, the term "packaging machine" refers to the complete packaging unit including the compartment, the motor and the component or any other attachment mechanism that connects the motor to the compartment. For example, the T4 packaging machine comprises the shell (the procapsid made primarily of gp23), the vertex portal protein (dodecameric gp20) and the gp17 packaging motor. The T4 DNA packaging machine is further described, for example, in Zhang et al., "A promiscuous DNA packaging machine from bacteriophage t4," *PLoS Biol.* 9(2):310000592 (2011), and in Rao et al., "DNA Packaging in Bacteriophage T4," *Madame Curie Bioscience Database*, Landes Bioscience, (2000), the entire contents and disclosures of which are incorporated herein by reference.

For purposes of the present invention, the term "packaging motor" refers to a molecular motor or a molecular machine that is capable of using chemical energy to drive the mechanical translocation of a nucleic acid and package the nucleic acid into a compartment. For example, the packaging motor in T4 bacteriophage uses the energy of ATP hydrolysis to translocate and package DNA into the capsid shell. The packaging motor may be a protein complex comprising one or more protein subunits and have enzymatic activities that help package nucleic acids, which include, but are not limited to ATPase, nuclease and translocase. For example, T4 bacteriophage packaging motor refers to a large terminase protein, the pentameric gene product (gp)17. The term "packaging motor" may also be considered to encompass additional proteins that regulate or enhance the activity of the actual motor. For example, the T4 packaging motor may also include a small terminase protein gp16. The T4 DNA packaging motor is further described in, for example, Sun et al., "The structure of the phage T4 DNA packaging motor suggests a mechanism dependent on electrostatic forces," *Cell* 135(7):1251-62 (2008), by reference.

For purposes of the present invention, the term "peptide-like" refers to short chain peptides as well as proteins, lipoproteins and glycoproteins, but will also, for convenience, include non-proteinaceous molecules, for example, amino acid-containing molecules. In certain embodiments, the peptide-like therapeutic agent may additionally comprise vitamins, steroids, azidothymidine, and free primaquine in addition to other agents. One useful class of peptides is immunomodulators such as interleukins, colony stimulating factors and interferons. Another useful class of proteins is antigens and immunogens such as are used in vaccines.

For purposes of the present invention, the term "purified" refers to the component in a relatively pure state—e.g. at least about 90% pure, or at least about 95% pure or at least about 98% pure.

For purposes of the present invention, the term "virus particle" refers to viruses and virus-like organisms.

DESCRIPTION

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein and references cited within them are incorporated herein by reference in their entireties including U.S. Provisional Patent Application No. 61/322,334 entitled a "A Promiscuous DNA Packaging Machine from Bacteriophage T4" filed Apr. 9, 2010.

Phage T4 is a prototype for tailed bacteriophages, the most abundant organisms on the planet, as well as for large eukaryotic viruses such as herpes viruses. These viruses encode powerful machines to package their genomes tightly inside an icosahedral-shaped capsid "head". Packaging into the capsid occurs via a dodecameric portal, localized in one of the vertexes of the capsid. Packaging requires precise orchestration of a series of steps: assembly of an empty prohead, concatemer cutting and attachment of the motor-DNA complex to the portal vertex, ATP-fueled DNA translocation until the head is full, DNA cutting to terminate packaging, detachment of the motor, and sealing of the packaged head by "neck" assembly. Sequential conformational changes, particularly in the portal, are thought to drive these transitions such that assembly proceeds directionally and irreversibly.

In one embodiment, the present invention takes advantage of the new discovered fact that the phage T4 packaging machine on various capsids is highly promiscuous, translocating DNA into proheads but also, unexpectedly, into previously filled virus heads. Other studies have shown that in filled viral capsids the structure of the portal is fundamentally altered, and it was thought that the packaging mechanism on full heads would be irreversible. An aspect of the invention relates to the showing that full heads, or heads that are emptied of most of their packaged DNA, can reassemble the packaging machine and use it to re-fill the capsid with any DNA molecules.

These results challenge the classic sequential virus assembly models, suggest an explanation for the evolution of viral genomes that fit capsid volume, and point the way to a novel nanocapsid delivery system in which the viral packaging machine (portal and motor) could be used to translocate DNA and other therapeutic molecules into synthetic capsids.

In one embodiment, the present invention provides a T4 bacteriophage component being used as a carrier to deliver nucleic acids and/or proteins of interest.

In one embodiment, the present invention provides a packaging motor that is a T4 bacteriophage packaging motor.

In one embodiment, the present invention provides a T4 packaging motor that can associate with a liposomal vesicle to package nucleic acids into the liposomal vesicle.

In one embodiment, the present invention provides a packaging motor that can associate with any compartment to which it is capable of attaching and package nucleic acids to the full volume capacity of the compartment.

In one embodiment, the present invention provides a multiuse type of delivery vehicle that can be packaged with nucleic acids and attached to proteins of interest.

Tailed bacteriophages are ubiquitously distributed in nature and are the most abundant organisms on the planet as referred to in Hendrix, "Evolution: the long evolutionary reach of viruses," *Curr. Biol.* 9: R914-R917 (1999). These, in particular, bacteriophage T4, are excellent models to elucidate the mechanisms of DNA condensation and decondensation in living organisms. The virion consists of a head into which the genome is packaged, and a tail that delivers the genome into the bacterial cell. The head is pressurized to ~6 MPa—equivalent to more than ten times the pressure inside a bottle of champagne—because of the packing of highly negatively charged, relatively rigid double-stranded DNA (dsDNA) to near crystalline density (~500 µg/ml) further described in Smith et al., "The bacteriophage straight phi29 portal motor can package DNA against a large internal force," *Nature* 413: 748-52 (2001); and Lander et al., "The structure of an infectious P22 virion shows the signal for headful DNA packaging," *Science* 312: 1791-95 (2006).

Common pathways and mechanisms are involved in building dsDNA viruses as described in Casjens, "Control mechanisms in dsDNA bacteriophage assembly," *The Bacteriophages*, Volume 1, Calendar R, editor, New York: Plenum Press, 15-91 (1988), Black et al., "Morphogenesis of the T4 head," *Molecular biology of bacteriophage T4*, Karam, editor, Washington, D.C.: American Society for Microbiology, 218-58 (1994), and Mettenleiter et al., "Herpesvirus assembly: an update," *Virus Res.* 143: 222-234 (2009). A capsid of precise dimensions is first assembled, often with a single type of protein subunit polymerizing around a protein scaffold (FIG. 1). A cone-shaped dodecameric portal initiates assembly and remains at the special five-fold vertex of the isometric capsid (prehead), facilitating all subsequent transactions: DNA entry, tail attachment, and DNA ejection as referred to in Simpson et al., "Structure of the bacteriophage phi29 DNA packaging motor," *Nature* 408: 745-50 (2000); and Lebedev et al. "Structural framework for DNA translocation via the viral portal protein," *EMBO J.* 26: 1984-94 (2007). The scaffold is removed, creating an empty space inside the capsid (prohead or procapsid) for encapsidating the viral genome (step A of FIG. 1). A packaging ATPase motor, also known as the "terminase," recognizes and cuts the concatemeric viral DNA and docks at the narrow protruding end of the prohead portal, inserting the DNA end into the ~3.5-nm portal channel as described in Rao et al., "The bacteriophage DNA packaging motor," *Annu. Rev. Genet.* 42: 647-81 (2008).

The packaging machine thus assembled drives DNA translocation utilizing the free energy of ATP hydrolysis (step B of FIG. 1). After filling the head ("headful" packaging), the motor cuts the DNA and dissociates from the DNA-full head (step C of FIG. 1) as referred to in Alam et al., "The headful packaging nuclease of bacteriophage T4," *Mol. Microbiol.* 69: 1180-90 (2008). The neck and tail proteins assemble on the portal, completing the infectious virus assembly (step D of FIG. 1) as described in Rao, "A virus DNA gate: zipping and unzipping the packed viral genome," *Proc. Natl. Acad. Sci.,* 106: 8403-04 (2009); Zheng et al., "A conformational switch in bacteriophage p22 portal protein primes genome injection," *Mol. Cell.* 29: 376-83 (2008); Bode et al., "The arrangement of DNA in lambda phage heads. I. Biological consequences of micrococcal nuclease attack on a portion of the chromosome exposed in tailless heads," *J. Mol. Biol.* 62: 493-502 (1971); Lhuillier et al., "Structure of bacteriophage SPP1 head-to-tail connection reveals mechanism for viral DNA gating," *Proc. Natl. Acad. Sci.* 106: 8507-12 (2009); and Edgar et al., "Morphogenesis of bacteriophage T4 in extracts of mutant-infected cells," *Proc. Natl. Acad. Sci.* 55: 498-505 (1966).

The phage T4 packaging motor is the fastest and most powerful reported to date. It generates ~60 pN of force and packages at a rate of up to 2,000 bp/s. The motor is composed of a large terminase protein, gp17 (70 kDa), and a small terminase protein, gp16 (18 kDa) as described in Rao et al., "Cloning, overexpression and purification of the terminase proteins gp16 and gp17 of bacteriophage T4. Construction of a defined in-vitro DNA packaging system using purified terminase proteins," *J. Mol. Biol.* 200: 475-88 (1988). gp17 contains all the enzymatic activities necessary for DNA packaging: ATPase, nuclease, and translocase as described in Leffers et al., "Biochemical characterization of an ATPase activity associated with the large packaging subunit gp17 from bacteriophage T4," *J. Biol. Chem.* 275: 37127-136 (2000); Rentas et al., "Defining the bacteriophage T4 DNA packaging machine: evidence for a C-terminal DNA cleavage domain in the large terminase/packaging protein gp17," *J. Mol. Biol.* 334: 37-52 (2003); and Baumann et al., "Isolation and characterization of T4 bacteriophage gp17 terminase, a large subunit multimer with enhanced ATPase activity," *J. Biol. Chem.* 278: 4618-27 (2003). Five molecules of gp17 assemble on the portal, forming a pentameric motor with a central translocation channel that is continuous with the portal channel as described in Sun et al., "The structure of the phage T4 DNA packaging motor suggests a mechanism dependent on electrostatic forces," *Cell* 135: 1251-1262 (2008). Gp16, a putative 1'-mer, regulates gp17's activities, but its location on the packaging machine is unknown as described in van Duijn, "Current limitations in native mass spectrometry based structural biology," *J. Am. Soc. Mass. Spectrom.* 21: 971-78 (2010); and Al-Zahrani et al., "The small terminase, gp16, of bacteriophage T4 is a regulator of the DNA packaging motor," *J. Biol Chem* 284: 24490-500 (2009). Structural and biochemical studies suggest that packaging is driven by the electrostatic force generated by the motor alternating between relaxed and tensed conformational states.

A fundamental feature of virus assembly is "sequential assembly" in which "simple" components assemble in a strict sequence to generate a complex nanomachine with unique biological properties. Each assembly step generates a new site or conformational state to which the next component binds with exquisite specificity, essentially irreversibly as described in Wood, "Bacteriophage T4 morphogenesis as a model for assembly of subcellular structure," *Q. Rev Biol.* 55: 353-67 (1980). A series of such steps, as documented by studies in phage T4, referred to in King, "Assembly of the tail of bacteriophage T4," *J. Mol. Biol.* 32: 231-62 (1968), and numerous other viruses leads to rapid and high-fidelity assembly of a complex infectious virion as described in Casjens et al., "Control mechanisms in dsDNA bacteriophage assembly," *The bacteriophages,* Volume 1, Calendar, editor, New York: Plenum Press, 15-91 (1988). In phage T4, this process assembles virions approaching a theoretical infection efficiency of 1.

The sequence of steps in the head morphogenesis of phage T4 (in vivo), as well as in other phages and dsDNA viruses (e.g., herpes viruses), is as follows: (i) assembly of the packaging motor on a nascent (unexpanded) empty prohead (step A of FIG. 1), (ii) expansion of the capsid after about 10%-25% of the genome is packaged (step B of FIG. 1), (iii) packaging until the head is full, (iv) cutting of DNA and dissociation of the motor (step C of FIG. 1), and (v) assembly of neck proteins to seal the packaged heads (step D of FIG. 1). Conformational changes in the portal are reported to drive these sequential irreversible transitions (FIG. 1; the portal goes through different conformational states in each stage)

An advantageous aspect of the invention relates to the assembly of the phage T4 genome packaging machine not strictly adhering to the paradigm of sequential and irreversible steps ("motor" refers to pentameric gp17; whereas "machine" refers to the complete packaging unit including shell [gp23], portal, and motor). Results show that the assembly of the phage T4 packaging machine is highly promiscuous and does not discriminate as to the type of head it assembles on. In one embodiment of the invention, the motor can translocate into the phage head, either the DNA-full head (step G of FIG. 1) or the once full but DNA-ejected head (step F of FIG. 1). In fact, the latter shows 5- to 10-fold greater packaging efficiency than the prohead. This is the first report demonstrating that a finished virus shell can reassemble the packaging machine and repackage any DNA. Single molecule optical tweezers experiments are used to show another embodiment of the invention, that the packaging rate of phage-head-assembled packaging machines is similar to that of machines assembled on packaging-naïve proheads. Single molecule fluorescence measurements show a further embodiment of the invention that the mature phage heads catalyze repeated packaging initiations, encapsidating multiple DNA molecules within the same head. An advantageous embodiment of the invention is that the phage T4 DNA packaging machine has unusual conformational plasticity, powering genome translocation into a passive capsid receptacle regardless of its maturation stage. These features may have driven the evolution of headful measured genomes in dsDNA viruses, and may offer avenues to further embodiments of the invention like the design novel nanodevices that can transport DNA therapeutics and vaccines into cells.

One of the central themes in virus assembly is sequential and irreversible assembly. Assembly of one component generates a new site or conformational state that is specific for the assembly of the next component and so on as further described in Casjens et al., "Control mechanisms in dsDNA bacteriophage assembly, *The bacteriophages,* Volume 1, Calendar, editor, New York: Plenum Press, 15-91 (1988); and King, "Assembly of the tail of bacteriophage T4," *J. Mol. Biol.* 32: 231-62 (1968). If a component is missing, assembly proceeds up to that point and stalls, accumulating a partially assembled structure and unassembled downstream components as further described in Edgar et al., "Morphogenesis of bacteriophage T4 in extracts of mutant-infected cells," *Proc. Natl. Acad. Sci.* 55: 498-505 (1966) and Kikuchi et al., "Genetic control of bacteriophage T4 baseplate morphogenesis. I. Sequential assembly of the major precursor, in vivo and in vitro," *J. Mol. Biol.* 99: 645-72 (1975). Although the precise mechanisms are still poorly understood, the assembled structure does not spontaneously disassemble, nor is it in equilibrium with the unassembled subunits, presumably because it is locked in a different, energetically stable, conformational state. This process not only ensures directional assembly in a predetermined order but also leads to rapid and high-fidelity construction of a complex infectious virion from the seemingly chaotic distribution of subunits in the infected cell.

Sequential conformational changes in the portal and the major capsid protein may drive maturation transitions from the nascent prohead to the DNA-full head as suggested in Casjens et al., "Control mechanisms in dsDNA bacteriophage assembly," *The bacteriophages*, Volume 1, Calendar, editor. New York: Plenum Press. 15-91 (1988); Black et al., "Morphogenesis of the T4 head," *Molecular biology of bacteriophage T4*, In: Karam, editor, Washington, D.C.: American Society for Microbiology, 218-58 (1994); and Rao, "A virus DNA gate: zipping and unzipping the packed viral genome," *Proc. Natl. Acad. Sci.* 106: 8403-404 (2009). These include assembly of the packaging motor, packaging initiation, prohead expansion, headful packaging, packaging termination, and assembly of neck proteins (FIG. 1, steps A to D).

The major capsid protein gp23 undergoes a major conformational change during prohead expansion, leading to a ~15% increase in outer dimensions and a ~50% increase in inner volume (gp23 is the cleaved form of the major capsid protein gp23; cleavage occurs during maturation of prohead to prohead; as indicated in FIG. 1, step A). A conformational change in the T4 portal gp20 was reported to trigger this expansion following assembly of packaging motor on the unexpanded prohead as referred to in Ray et al., "Portal control of viral prohead expansion and DNA packaging," *Virology* 391: 44-50 (1999). About 870 binding sites for Soc (small outer capsid protein) and 155 binding sites for Hoc (highly antigenic outer capsid protein) are exposed following the expansion transition as described in Carrascosa, "Head maturation pathway of bacteriophages T4 and T2. IV. In vitro transformation of T4 head-related particles produced by mutants in gene 17 to capsid-like structures," *J. Virol.* 26: 420-28 (1978).

In phages SPP1 and P22, portal conformational variants were shown to either underpackage (~95% of genome per head), or overpackage (~105% of genome per head) the head as referred to in Orlova et al., "Structure of the 13-fold symmetric portal protein of bacteriophage SPP1," *Nat. Struct. Biol.* 6: 842-846 (1999); and Casjens et al., "Bacteriophage P22 portal protein is part of the gauge that regulates packing density of intravirion DNA," *J. Mol. Biol.* 224: 1055-74 (1992). In phage P22, a piece of packaged DNA spools around the portal, forcing a conformational change that apparently signals the motor to make the headful termination cut and disengage from the DNA-full head. Another portal conformational change primes DNA delivery following the binding of neck proteins. Thus, as was appreciate in the art at the time of the invention, the DNA-full heads, having just ejected the packaging motor following head filling, would not be competent to reinitiate packaging; instead, these would be primed to bind the neck proteins. Applicants show that, for the first time, the packaging machine assembly is neither sequential nor irreversible. It can occur on the finished head as efficiently as on the packaging-naïve empty (unexpanded or expanded) prohead, as was demonstrated by bulk as well as single molecule experiments. Such promiscuous assembly appears to be a special property of the packaging machine because all other head assembly transitions (for example, head expansion) are irreversible and follow the classic sequential assembly paradigm. The fact that the motor can translocate DNA into the capsid regardless of its maturation state—unexpanded, expanded, DNA-full, or DNA-ejected—suggests that the shell as such is a passive receptacle. The main goal of the packaging process appears to be to power genome into a capsid receptacle until it is full.

What is the structural basis for the conformational plasticity of the packaging machine? X-ray and cryo-electron microscopy structures show that despite lacking sequence similarity, the three-dimensional structure of the portals is strictly conserved as described in Mettenleiter et al., "Herpesvirus assembly: an update," *Virus. Res.* 143: 222-34 (2009) and Simpson et al., "Structure of the bacteriophage phi29 DNA packaging motor," *Nature* 408: 745-750 (2000). The cone-shaped portal consists of three parts: a wide domain that is inside the icosahedral vertex, a long central stem that forms the channel, and a stalk that protrudes out of the capsid. The channel is lined by α-helices radiating from the center at a ~45° angle, whereas the protruding end has an α/β domain connected by loops. In one model, the portal may oscillate between different energetically equivalent conformational states but gets "frozen" in one state upon binding to a partner molecule, gp17, gp13, etc. In another model, different binding sites may be accessible at different stages of the maturation pathway. In the nascent procapsid, only the protruding stalk would be accessed, allowing the assembly of gp17, but after head filling, the internal pressure of packaged DNA might push the portal down, exposing part of the stem that contains binding sites for neck proteins. Neck protein assembly displaces the packaging motor, but in the absence of neck proteins the packaging motor can reassemble to the portal.

A promiscuous packaging machine may have led to the evolution of headful genomes, a fundamentally common feature among dsDNA phages and viruses, including the herpes viruses as referred to in Rao et al., "The bacteriophage DNA packaging motor," *Annu. Rev. Genet.* 42: 647-81 (2008). Closed shells assembled from an ancient capsid protein probably predates genome evolution. A flexible packaging machine that can indiscriminately translocate DNA molecules into a capsid receptacle would continue packaging until the capsid is full. The filled shells, by virtue of the energy (internal pressure) present in the tightly packed DNA, can more efficiently deliver the "genome" into a host cell. Eventually, this selective advantage leads to the evolution of infectious capsids (virions) whose interior is tightly packed with DNA, their length dictated by the internal volume of the closed shell. An advantageous embodiment of the invention is to tightly package DNA to efficiently deliver exogenous material into a host cell, under either in vitro or in vivo conditions.

The conformational flexibility of the packaging machine may also lead to more efficient production of infectious virions in a normal infection. The low-abundant packaging/terminase proteins must compete for the DNA substrate with a variety of other DNA metabolizing enzymes involved in transcription, replication, recombination, and repair. Should the packaging motor prematurely fall off, or be displaced from the head, it could reassemble and resume packaging.

In another embodiment of the invention, highly stable virus shells are used as packaging containers. This is a significant breakthrough from a technical standpoint and has broad implications. First, the proheads currently used in all the in vitro DNA packaging systems are very fragile, and in T4 the prohead is a heterogeneous mixture of unexpanded, expanded, damaged, and partially Soc/Hoc-bound particles. In an embodiment of the invention, the heads that have undergone all the maturation transitions are homogenous and structurally very stable and reinforced with 870 copies of Soc, offering a very efficient system to package DNA as well as generate high-resolution reconstructions of packaging intermediates. Another embodiment of the invention is that partial heads have 5- to 10-fold greater packaging efficiency than the proheads. In an advantageous embodiment of the invention, it is possible to overcome some of the technical barriers to developing in vitro DNA packaging systems for eukaryotic viruses such as herpes viruses and adenoviruses by ejecting the packaged DNA from the virions as described in Newcomb et al., "Polarized DNA ejection from the herpesvirus capsid," *J. Mol. Biol.* 392: 885-94 (2009), and repackaging different DNA into the emptied heads. In another embodiment of the invention, the powerful packaging motor can be used to encapsidate large chunks of foreign DNA and target these particles to specific cells or tissues by displaying specific ligands on the capsid surface as referred to in Li et al., "Bacteriophage T4 capsid: a unique platform for efficient surface assembly of macromolecular complexes," *J. Mol. Biol.* 363: 577-88 (2006). Such particles can deliver multiple genes for gene therapy as well as multivalent DNA vaccines against pathogenic agents. In a further embodiment of the invention the phage T4 head, which has very high capacity (~170 kb) and demonstrates ability to package multiple DNA molecules in the same head, would be a particularly attractive nanoparticle. In another embodiment of the invention, nanomotors are designed for various biomedical applications. Since the shell appears to be a passive receptacle, the packaging machine (portal and motor) could be stripped off of the capsid and inserted into an artificial and much larger shell, such as a liposome or mammalian cell, and the machine could be made to translocate DNA and other therapeutic molecules into these compartments.

The surface of bacteriophage T4 nanoparticles can be modified, either through genetic engineering or direct chemical conjugation to display functional moieties such as antibodies or other proteins to recognize a specific target and can be used as sensors as further described in Archer et al., *Sensors*, 9, 6298-311 (2009). Among the broad range of plant and bacterial viruses that have been investigated, the interest in the use phages and particularly bacteriophage T4 as a nanomaterial, has recently increased, due to its flexible, unrestricted display system Rao, V. B. Methods and compositions comprising bacteriophage nanoparticles as has been described in U.S. Patent Application. No. 2005/0226892 to Rao, entitled, "Methods and compositions comprising bacteriophage nanoparticles," published Oct. 13, 2005; Li et al., "Assembly of the small outer capsid protein, Soc, on Bacteriophage T4: A novel system for high density display of multiple large anthrax toxins and foreign proteins on phage capsid," *J. Mol. Biol.* 370, 1006-1019 2007; Wu et al., "Bacteriophage T4 nanoparticle capsid surface SOC and HOC bipartite display with enhanced classical swine fever virus immunogenicity: A powerful immunological approach," *J. Virol. Meth.* 139, 50-60 (2007).

Liposomes can be prepared in many different sizes, ranging from small unilamellar vesicles (SW's), whose smallest dia. are about 20 nm, to giant unilamellar vesicles (GUV's) up to tens of pm in dia. In between are the multilamellar vesicles (MLV's); i.e. the first generation of liposomes (1), of several hundreds of nm in dia., and the more recent large unilamellar vesicles (LUV's), characterized by high capture volumes, whose dia. can be adjusted (e.g. 100 or 200 nm) and size distribution narrowed-down by extrusion through specific membranes (2). In essence, liposomes are highly versatile structures whose properties can be modulated by changing number of parameters such as size, lamellarity, composition of the bilayers, surface charges and surface properties; for the chemist the (phospho)lipids which are the constituents of liposomes are also challenging molecules for designing analogs endowed with new properties and derivatives that are useful: e.g., for coupling ligands to the surface of the vesicles. Because of the polyanionic nature of DNA, cationic (and neutral) lipids are typically used for gene delivery, while the use of anionic liposomes has been fairly restricted to the delivery of other therapeutic macromolecules as referred to in Mayhew et al., "Therapeutic applications of liposomes," *Liposomes*, Ostro, editor, Marcel Dekker: New York, 289-341 (1983).

In another embodiment of the invention, a carrier that encompasses bacteriophage T4 viruses or the T4 virus capsid can have mutations in any of the constituent protein subunits that may result in advantageous properties in methods of gene therapy. The mutations may be introduced into the nucleic acid sequences of the constituent carrier proteins. The carrier may also be used to deliver target genes or proteins that have also be modified. For example, modifications can address issues like the short-lived nature of gene therapy by generating nucleic acids that are long lived and stable. Another modification can result in no or reduced immune responses from the organism when exogenous material is introduced into it. In addition, modifications can be made to address toxicity, immune and inflammatory responses and potential disease causing ability of the carrier itself. Modification can also be made to address multigene disorders and to reduce the chance of tumor formation with insertional mutagenesis. The terms "protein," "peptide," "polypeptide," and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The present invention also encompasses carriers into which polypeptides with novel functions are introduced. For example, the novel function may proceed via directed or random mutagenesis coupled with a functional selection or screen. Methods of mutagenesis are well known to one of skill in the art. As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be associated with the present invention. The term "recombinant" means a nucleotide sequence that has been manipulated "by man" and that does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized: for example, the codons may be optimized for human use. In preferred embodiments the nucleotide sequences of the invention are both mutated to abrogate the normal in vivo function of the encoded proteins, and codon optimized for human use.

As regards codon optimization, the nucleic acid molecules associated with the invention have a nucleotide sequence that encodes the antigens of the invention and can be designed to employ codons that are used in the genes of the subject in which the antigen is to be produced. In a preferred embodiment, the codons used are "humanized" codons, i.e., the codons are those that appear frequently in highly expressed human genes as described in Andre et al., "Increased immune response elicited by DNA vaccination with a synthetic gp120 sequence with optimized codon usage," *J. Virol.* 72:1497-1503 (1998). Any suitable method of codon optimization may be used. Such methods, and the selection of such methods, are well known to those of skill in the art. In addition, there are several companies that will optimize codons of sequences, such as Geneart and its website of the same name. Thus, the nucleotide sequences utilized in the invention can readily be codon optimized.

Another embodiment of the invention also encompasses nucleotide sequences that encode functional and/or equivalent variants and derivatives of the proteins that constitute the carrier or proteins that are attached to the carrier or are being delivered by the carrier of the invention and functionally equivalent fragments thereof. For instance, changes in a DNA sequence that do not change the encoded amino acid sequence, as well as those that result in conservative substitutions of amino acid residues, one or a few amino acid deletions or additions, and substitution of amino acid residues by amino acid analogs are those that will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin et al., "Methods for assessing the statistical significance of molecular sequence features by using general scoring schemes" *Proc. Natl. Acad. Sci.* 87: 2264-68 (1990), modified as in Karlin et al., "Applications and statistics for multiple high-scoring segments in molecular sequences," *Proc. Natl. Acad. Sci.* 90: 5873-77 (1993).

Another example of a mathematical algorithm used for comparison of sequences is the algorithm of Myers et al., "Optimal alignments in linear space," *CABIOS* 4: 11-17 (1988). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson et al., "Improved tools for biological sequence comparison," *Proc. Natl. Acad. Sci.* 85: 2444-48 (1988).

Advantageous for use according to the present invention is the WU-BLAST (Washington University BLAST) version 2.0 software. WU-BLAST version 2.0 executable programs for several UNIX platforms can be downloaded from on-line. This program is based on WU-BLAST version 1.4, which in turn is based on the public domain NCBI-BLAST version 1.4 described in Altschul et al., "Local alignment statistics," *Methods in Enzymology*, Doolittle ed., 266: 460-80 (1996); Altschul et al., *J. Mol. Biol.*, 215: 403-410 (1990); Gish et al., *Nature Genetics* 3: 266-272 (1993); and Karlin et al., *Proc. Natl. Acad. Sci.* 90: 5873-5877 (1993), the entire contents and disclosures of which are incorporated herein by reference.

The various recombinant nucleotide sequences and polypeptides associated with the invention are made using standard recombinant DNA and cloning techniques. Such techniques are well known to those of skill in the art. See, for example, Sambrook et al., *Molecular Cloning: A Laboratory Manual*, second edition, volume 1, 2 and 3 (1989).

In certain embodiments, the polypeptides associated with the present invention may be used in vitro (such as using cell-free expression systems) and/or in cultured cells grown in vitro in order to produce the polypeptides which may then be used for various applications such as in the production of proteinaceous vaccines. For applications where it is desired that the polypeptides be expressed in vivo, for example when the transgenes of the invention are used in DNA or DNA-containing vaccines, any vector that allows for the expression of the polypeptides of the present invention and is safe for use in vivo may be used.

For the polypeptides associated with the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

The description of the present invention is enhanced by the various examples that follow.

Example 1

Phage heads reassemble a functional DNA packaging machine and package DNA. Phage T4 gp10 in association with gp11 forms the tail-pins of the baseplate as described in Leiman et al., "Structure and morphogenesis of bacteriophage T4," *Cell. Mol. Life. Sci.* 60: 2356-70 (2003). Since the tail-pin assembly is the first step of tail assembly, tail structures do not assemble in the absence of gp10. The proteins gp13, gp14, and gp15 assemble into a neck that seals off packaged heads, with the gp13 protein directly interacting with the portal protein gp20 following DNA packaging and gp14 and gp15 then assembling on the gp13 platform. 10am13 am mutants (and analogous mutants in phage λ and other phages) complete all the packaging steps including the cutting of concatemeric DNA and dissociation of the packaging motor. DNA-full phage heads accumulate in the 10am13 am mutant infected cells, which can be converted to infectious virions by in vitro complementation with neck and tail proteins. Thus, according to the well-accepted sequential assembly models, the heads following completion of DNA packaging are expected to have the least affinity for the packaging motor but high affinity for the neck proteins. A novel aspect of the invention relates to it being the first time that the packaging machine does not discriminate between "prohead" (FIG. 1, step A) and finished or matured "phage head" (steps F and G of FIG. 1).

Figure 2:
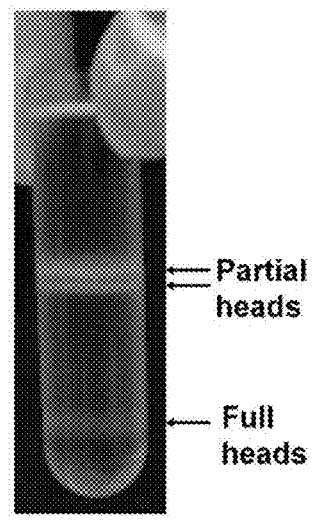
FIG. 2 is a photo showing the isolation of phage heads by differential centrifugation followed by CsCl gradient centrifugation.
Figure 3:
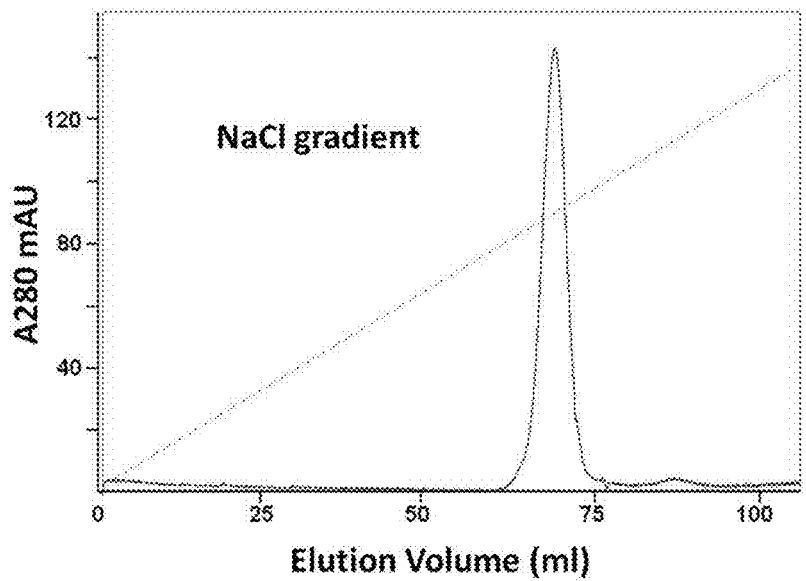
FIG. 3 is a graph showing the peak associated with purification of partial heads by DEAE-Sepharose column chromatography.
Figure 6:
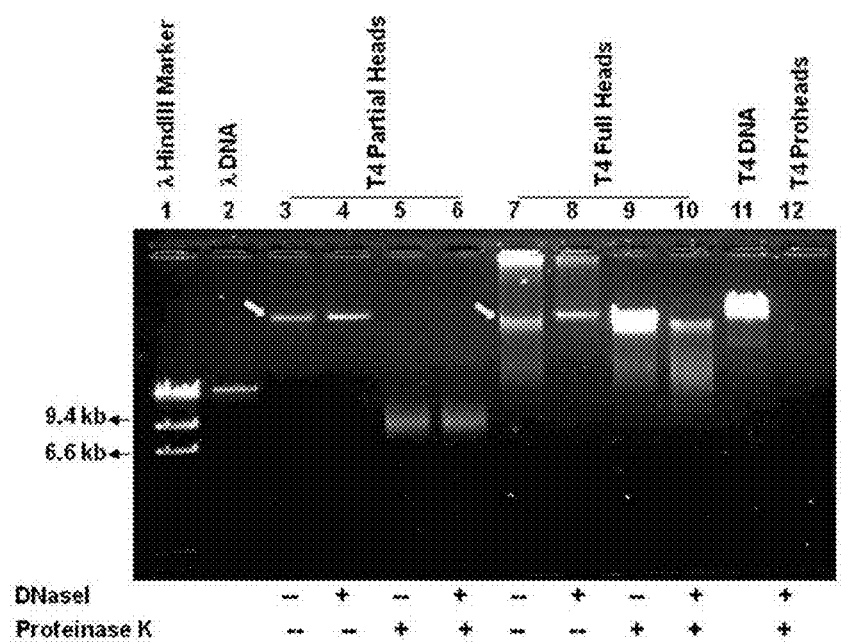
FIG. 6 is an image of a gel showing phage heads treated with DNAse I and/or proteinase K and subjected to agarose gel electrophoresis and stained with cyber green.

The 10am13 am heads are separated into two major species by CsCl density gradient centrifugation (DNA sequencing shows that the 10am13 am phage has TAG amber mutations at residues Trp 430 in gene 10 and Gln 39 in gene 13). Two very closely spaced low-density bands are present at about the middle of the gradient, and a high-density band is located near the bottom of the gradient (FIG. 2). The two close bands, making about 93% of the total heads, contain the same head species but migrate slightly differently, probably because the heads in the upper band ate loosely associated with cell debris (in some purifications, only a broad single band is seen). Upon further purification by diethylaminoethyl cellulose (DEAE) ion-exchange chromatography, the cell debris contaminants are removed and the heads elute as a single symmetrical peak (FIG. 3). Both the head species are resistant to SDS at room temperature (FIG. 4), which means that they are, as expected, in the fully expanded state. Agarose gel electrophoresis shows that the low-density heads contain a ~8-kb DNA band (FIG. 6, lanes 5 and 6) whereas the high-density heads contain near genome length DNA (FIG. 6, lanes 9 and 10). The former is referred to as "partial" heads and the latter as "full" heads.

Since 13 am mutants accumulate DNA-full heads, the partial heads likely arose by spontaneous ejection of the packaged DNA from full heads during the purification procedures. The full heads are known to be unstable and to spontaneously eject the DNA unless sealed off by neck proteins. The ejected DNA may be digested by the DNAse I present in the buffer, leaving only a small piece of DNA inside the shell. As seen in FIG. 6, the DNA that associates with the partial heads was inside the head because it comigrates with the head band (lane 3) and is resistant to DNAse I treatment (lane 4), but upon digestion with proteinase K, the DNA is released and migrates to the 8-kb position (lane 5). It is interesting that the 8-kb band is consistently observed in several independent preparations and is quite compact, suggesting that ejection stops within a narrow window, after about 95% of the genome is released. This DNA may belong to a specific sequence of the T4 genome because it binds to the capsid protein and is not ejected. To test this hypothesis, the DNA is extracted from partial heads by phenol and chloroform and digested with the restriction enzymes EcoRV (six-base cutter) or TaqI (four-base cutter), which can cut the hydroxymethylated and glycosylated T4 DNA. If the 8-kb DNA belongs to a unique sequence of T4 genome, a series of discrete bands should result. Alternatively, if each 8-kb piece belongs to a different part of the genome, the restriction fragments should not form discrete bands. Results indicate that the products migrate as a smear, demonstrating that the retained DNA does not have a unique sequence. This is also consistent with the fact that the ends of the T4 genome are nearly random, and thus it is not expected that the stretch of the genome that is in proximity to the capsid protein will be of the same DNA in different particles.

The full heads, which make up to about 7% of the total heads, have the packaged genome relatively stably retained inside the head, presumably because either the portal channel is constrained as suggested in Lander et al., "The structure of an infectious P22 virion shows the signal for headful DNA packaging," *Science* 312: 1791-95 (2006) or the DNA ends are not in close proximity to the entrance of the portal channel. These heads slowly release DNA upon storage at 4° C.

Figure 4:
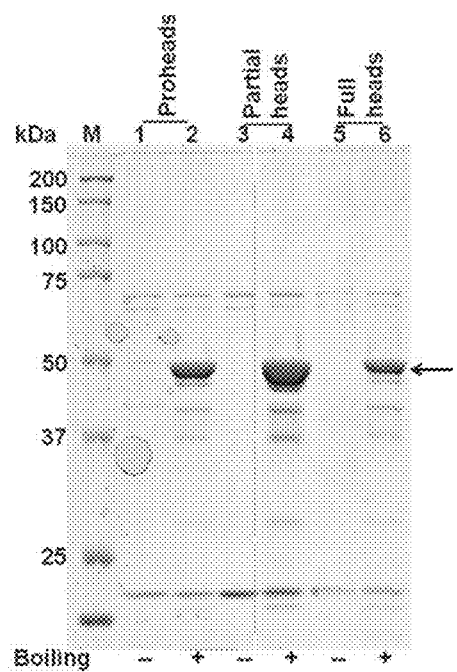
FIG. 4 is an image of an SDS-PAGE gel showing separation of heads at different stages.
Figure 5:
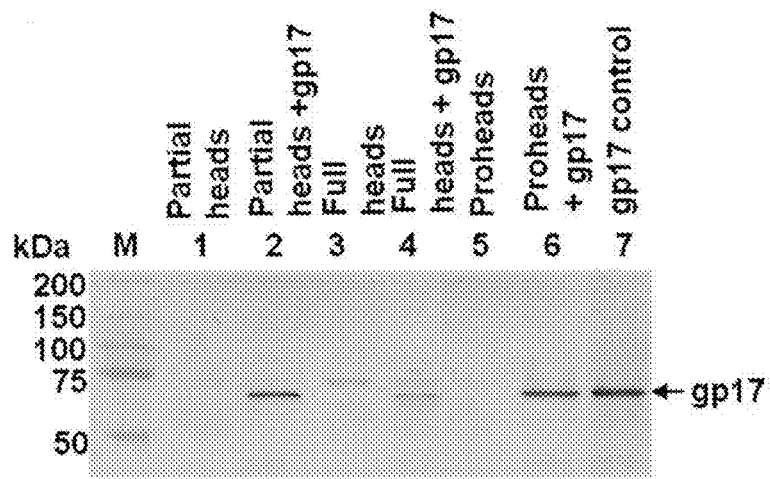
FIG. 5 is an image of a western blot membrane probed with Gp17 antibodies.
Figure 7:
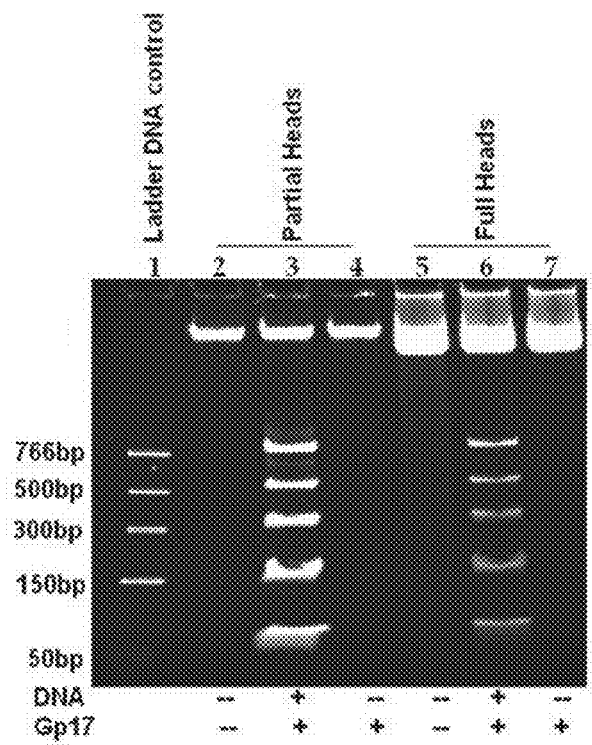
FIG. 7 is an image of a gel showing the packaging of short DNA fragments into phage heads under different conditions like with and without DNA and with and without Gp17.

The packaging activity of partial and full heads is determined by in vitro DNA packaging assay, using the 17am18amrII empty proheads as a positive control. In phage T4, the empty proheads produced by packaging-defective 17 am mutant infections are mostly of the expanded type (see lanes 1 and 2 of FIG. 4) since expansion occurs spontaneously when packaging is blocked in vivo. The resultant packaging-naïve empty expanded proheads, which package DNA as well or better than the unexpanded proheads, have been used as a positive control in the packaging assays as referred to in Rao et al., "DNA packaging of bacteriophage T4 proheads in vitro. Evidence that prohead expansion is not coupled to DNA packaging," *J. Mol. Biol.* 185: 565-578 (1985); Black et al., "Mechanistic coupling of bacteriophage T4 DNA packaging to components of the replication-dependent late transcription machinery," *J. Biol. Chem.* 281: 25635-25643 (2006); and Kondabagil et al., "The DNA translocating ATPase of bacteriophage T4 packaging motor," *J. Mol. Biol.* 363: 786-99 (2006). In bulk packaging assays, both partial and full heads efficiently pack short DNA fragments (50-766 bp) (FIG. 7). Packaging efficiency of partial heads is about six times higher than that of the proheads, the true precursors of DNA packaging in vivo (packaging efficiency is defined as the number of DNA molecules packaged per number of head particles). This may be because the proheads, unlike the mature heads, are fragile and might have been damaged during purification because of irregular expansion in vitro and/or lack of the stabilizing capsid decoration proteins Soc and Hoc as referred to in Fokine et al., "Molecular architecture of the prolate head of bacteriophage T4," *Proc Natl. Acad. Sci.* 101: 6003-08 (2004). The efficiency of partial head packaging is about five to ten times higher than that of the full heads (FIG. 7, lanes 3 and 6), which maybe because most of the full heads may not have any empty space left to accommodate additional DNA. Accordingly, the partial heads, but not the full heads, packaged the 48.5-kb phage λ DNA (FIG. 8, lanes 7 and 15) or the T4 genomic DNA. To confirm that the partial and full heads reassemble the exogenously added packaging motor, the head-gp17 complexes are purified and analyzed by Western blotting using polyclonal gp17 antibodies. It is seen that both types of heads reassemble the externally added gp17 (FIG. 5). The above findings are reproduced by constructing additional 10am13 am phage mutants in which either hoc or soc, or both genes, are also deleted.

FIG. 1 shows the major capsid protein assembles around a scaffolding core into a prehead. The core is removed by proteolysis to produce an empty unexpanded prohead (A). The unexpanded prohead normally has a round shape, but in phage T4 it has angular geometry as referred to in Steven et al., "Conformational changes of a viral capsid protein. Thermodynamic rationale for proteolytic regulation of bacteriophage T4 capsid expansion, co-operativity, and super-stabilization by soc binding," *J. Mol. Biol.* 228: 870-84 (1992). The packaging motor-DNA complex docks on portal and initiates packaging. The prohead expands after about 10%-25% of the DNA is packaged (B). After headful packaging, the motor cuts the concatemeric DNA and dissociates from the DNA-full head (C). The neck proteins (gp13, gp14, and gp15) assemble on portal to seal off the DNA-full head and provide a platform for tail assembly (D). The various colors of portal represent different conformational states. In promiscuous assembly, the packaging motor assembles on a partial head produced by ejection of packaged DNA (E) or a full head (G), and refills the head with new fragments of DNA ([F] and [G]; new DNA fragments are shown attached to the motor in both the full and partial head stages).

FIG. 2 shows The 10am13 am heads isolated by differential centrifugation followed by CsCl gradient centrifugation as described in Example 5. The two closely spaced bands at the top of the gradient contained partial heads that had ejected most of their packaged DNA, save an ~8-kb piece. The band at the bottom of the gradient contained full heads in which the packaged T4 genome is stabilized. FIG. 3 shows the purification of partial heads by DEAE-Sepharose column chromatography. The two closely spaced head bands at the top of the CsCl gradient are pooled, dialyzed against 10 mM Tris-HCl (pH 7.5), 50 mM NaCl, and 5 mM MgCl2, and purified by ion-exchange chromatography (AKTA Prime, GE Healthcare). The column is pre-equilibrated with 50 mM Tris-HCl (pH 7.5) and 5 mM MgCl2, and a linear gradient of 0-300 mM NaCl was applied to elute the bound heads. The peak fractions are pooled, concentrated by filtration, and stored at 4° C. FIG. 4 shows the partial and full heads fully expanded. The purified proheads, partial heads, and full heads are mixed with SDS gel loading buffer and kept at room temperature ("−") or boiling temperature ("+") for 5 min. The samples are then separated by 10% SDS-PAGE, stained with Coomassie blue R, and destained. Note that the major capsid protein, gp23* (position marked with arrow), was not seen in the room temperature samples because the expanded heads could not be dissociated into gp23* subunits. FIG. 5 shows partial and full heads reassembled with the exogenous gp17. About 5×10¹¹ proheads, partial heads, or full heads are incubated with purified gp17-K577 (0.3 µM; 50:1 ratio of gp17 molecules to gp20 subunits) in a buffer containing 50 mM Tris-HCl (pH 7.5), 100 mM NaCl, and 5 mM MgCl2, at room temperature for 30 min. The head-gp17 complexes are sedimented by centrifugation at 18,000 rpm for 45 min, and the pellet is washed several times to remove any unbound gp17. The proteins are transferred to PVDF membrane, and Western blotting is performed using polyclonal gp17 antibodies. The results are confirmed by doing the same experiment with full-length gp17 and a GFP-gp17 fusion protein. Only the gp17-K577 (C-terminal 33 amino acids of gp17 are deleted) data are shown because gp17-K577 is protease resistant and migrates as a single band as opposed to three bands with the full-length gp17 and GFP-gp17, and also because there is no background overlapping band at the same position. The gp17 band in the full head lane (lane 4) is faint because some of these heads release the packaged DNA during the procedure, which result in poor recovery of the heads during the centrifugation and washing steps.

Figure 8:
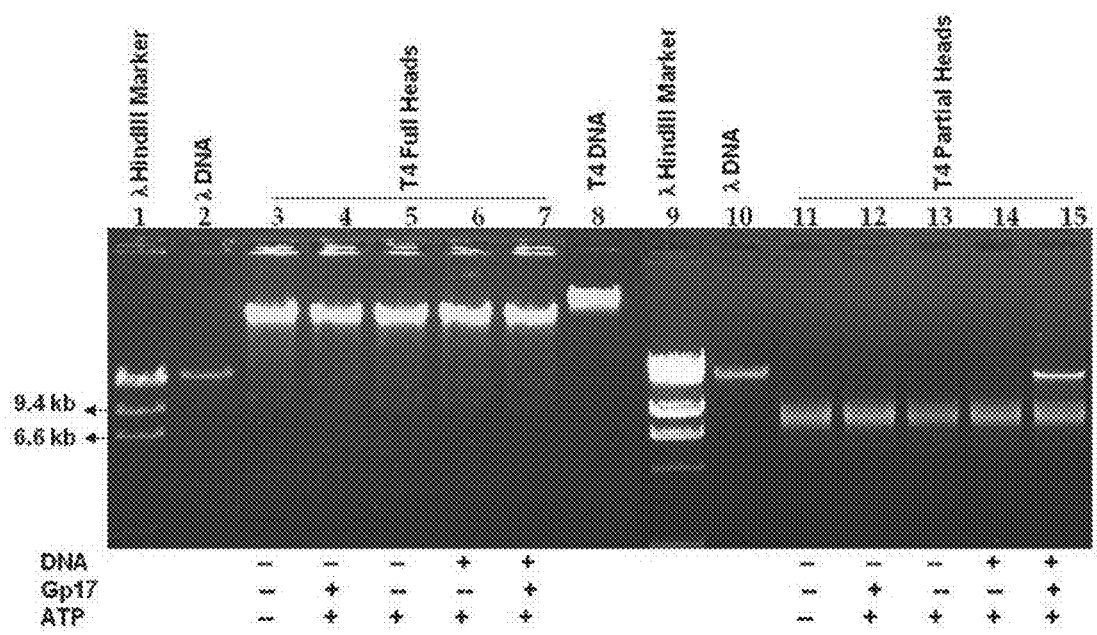
FIG. 8 is an image of a gel showing the packaging of short DNA fragments into phage heads under different conditions like with and without DNA, with and without Gp17 and with and without ATP.

FIG. 6 shows partial heads (lanes 3-6), full heads (lanes 7-10), or proheads (lane 12) are treated with DNAse I (37° C., 30 min) and/or proteinase K (65° C., 30 min), as shown by "+" or "−" rows under the figure, and subjected to agarose gel (0.8% w/v) electrophoresis and stained with cyber green. The molecular size markers λ HindIII (lane 1), λ DNA (lane 2), and T4 DNA (lane 11) are used to determine the size of the DNA present in the heads. Partial head lanes 3-6: lane 3, without any treatment; lane 4, treated with DNAse I; lane 5, treated with proteinase K; lane 6, treated first with DNAse I and then with proteinase K. Arrow shows the position of the heads stained with cyber green because they are associated with a ~8-kb DNA (lane 3). The 8-kb DNA is inside the heads because it is resistant to DNAse I treatment (lane 4) but releases by treatment with proteinase K (lanes 5 and 6). Full head lanes 7-10: lane 7, without any treatment; lane 8, treated with DNAse I; lane 9, treated with proteinase K; lane 10, treated first with DNAse I and then with proteinase K. Note that the untreated full heads show, in addition to the head band (arrow), an intensely stained band in the well plus a smear (lane 7), both of which are removed by digestion with DNAse I (lane 8). This is because some of the full heads extruded the packaged DNA during storage, which remained complexed with the head and retained in the well. This is confirmed by treatment with proteinase K, which releases this DNA as well as that packaged inside, producing a single band (lane 9). Treatment first with DNAse I results in the digestion of the outside DNA, and subsequent addition of proteinase K digests the capsids and releases the DNA packaged inside (lane 10). The DNA in lanes 9 and 10 is slightly shorter than that isolated from phage (lane 11), presumably because a segment of packaged DNA near the portal was accessible to DNAse I digestion [11], [13], [14]. Arrow shows the position of the heads stained with cyber green because they are associated with DNA inside the head (lane 7). The control 17am18amrII proheads are empty and showed no staining with cyber green (lane 12) (FIGS. 7 and 8). Packaging of short DNA fragments (50-766 bp) (FIG. 7), or λ DNA (48.5 kb) (FIG. 8) under various reaction conditions, as shown under the figure.

Example 2

Single mature-phage-head-assembled packaging machines refill the capsid. Although Example 1 shows that full heads package DNA, it may be argued that a fraction of the full heads ejected DNA during CsCl gradient centrifugation, converting them into partial heads. To address this question, 10am13 am heads are prepared without the CsCl gradient centrifugation. The infected cells are lysed in the presence of DNAse I, and phage heads are isolated by differential centrifugation. These heads, which contain a mixture of partial heads and full heads, are packaged with DNA (50- to 766-bp ladder fragments) and are then separated by CsCl density gradient centrifugation. This not only minimized any DNA ejection from full heads but, more importantly, ensures that only the full heads that package DNA sediment to the high-density position (lower band) in the CsCl gradient.

Figure 9:
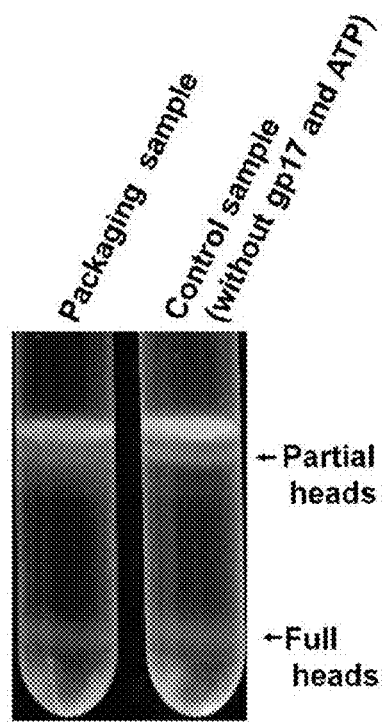
FIG. 9 is an image showing the gradient following differential centrifugation of phage heads that were lysed in the presence of DNAase.
Figure 10:
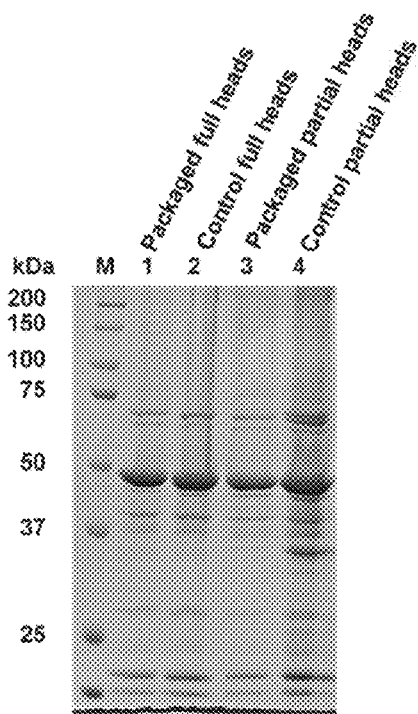
FIG. 10 is an image of an SDS-PAGE gel showing the concentration of particles used in the packaging reactions.

The partial and full head bands (FIG. 9) are extracted from the CsCl gradient, treated with proteinase K to release packaged DNA, and electrophoresed on a 4%-20% polyacrylamide gel. The samples are also electrophoresed prior to proteinase K treatment on an SDS polyacrylamide gel to determine the number of head particles (FIG. 10). As shown in FIG. 11, the full heads package the ladder DNA fragments at similar efficiency as the gradient-purified full heads shown in FIGS. 6, 7 and 8 did. Control samples in which the heads are treated the same way except that gp17 and ATP are omitted in the packaging reactions showed no detectable DNA (FIG. 11, compare packaged lanes 1 and 2 to control lanes 3 and 4). The partial heads, as expected, also package DNA at a similar efficiency as the gradient-purified partial heads (FIGS. 6, 7 and 8). Indeed, the packaged partial head band shows a downward shift towards higher density after packaging (see the packaged left gradient tube in FIG. 9 showing broadening of partial head band towards higher density when compared to the control gradient tube on the right). These experiments indicate that there are no fundamental barriers to packaging short pieces of DNA into full heads, an observation further confirmed by single molecule optical tweezers experiments.

FIG. 9 shows the phage heads are isolated from 10am13 am infected *E. coli* P301 cells (500 ml culture) by lysis in the presence of DNAse I followed by differential centrifugation. The phage head pellet containing a mixture of partial heads and full heads is resuspended in 200 µl of 50 mM Tris-HCl (pH 7.5) and 5 mM MgCl2. The sample is split into two halves, and larger scale packaging assays are conducted immediately. The 500-µl packaging reactions contained 100 µl of phage heads, 4.75 µM GFP-gp17, 43 µg of ladder DNA (50-766 bp; NEB), 5% PEG buffer, and 1 mM ATP. Gp17 and ATP are omitted in the control reaction. After 30 min. of incubation at room temperature, 40 µl (1,000 units) of Benzonase nuclease (EMD Biosciences) is added to digest unpackaged DNA, and the samples are separated by CsCl density gradient centrifugation. FIG. 10 shows the partial and full head samples from the gradient are electrophoresed on 10% SDS polyacrylamide gel to analyze for proteins and to estimate the concentration of particles used in the packaging reactions. Since the concentration of full heads is very low compared to that of partial heads (roughly 1/10th that of partial heads), the full heads are concentrated by high-speed centrifugation such that the number of particles per lane are approximately the same for both full heads and partial heads (FIGS. 11 and 12). The full (FIG. 11) and partial (FIG. 12) head bands from the gradient are treated with proteinase K (18.5 µg; Fermentas) and electrophoresed on 4%-20% polyacrylamide gel in Tris-borate buffer (pH 8) to analyze for packaged DNA.

Example 3

Figure 13:
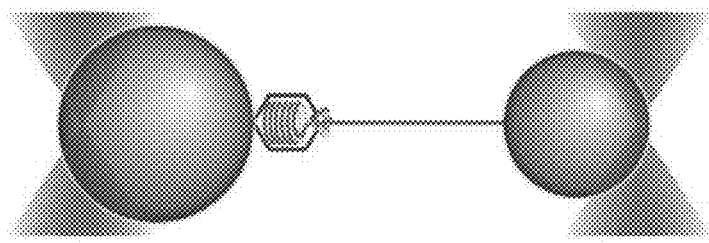
FIG. 13 is a schematic illustration showing the dual optical trap setup for single molecule DNA packaging.

Single mature-phage-head-assembled packaging machines refill the capsid. Single molecule experiments are conducted using dual-trap optical tweezers in a "force-clamp" mode. Head-gp17 packaging complexes are formed in the presence of the non-hydrolyzable analog, ATP-γ-S, and immobilized on T4-antibody-coated microspheres. The substrate DNA molecules (10 kb) biotinylated at one end are attached to streptavidin-coated microspheres. The microspheres are captured in separate traps and brought into near contact and quickly separated (FIG. 13). This "fishing" procedure is repeated until a tether was formed, as evident by a rise in force when the motor captures the DNA. A constant force of 5 pN is then applied by a feedback loop, and packaging is measured as decrease in tether length as a function of time.

Figure 14:
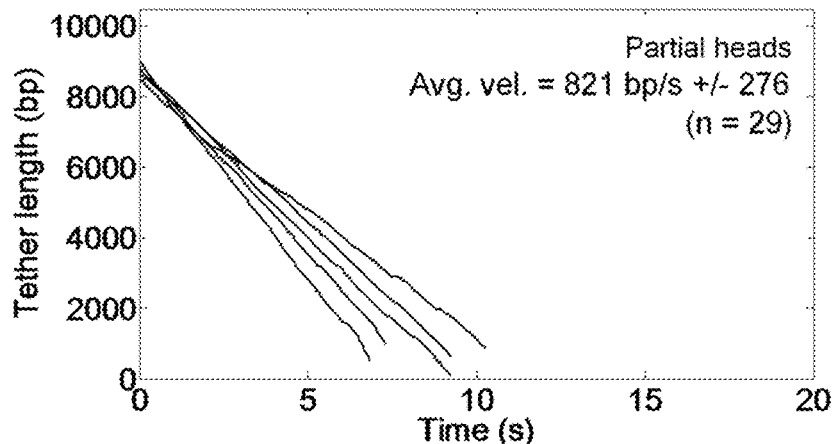
FIG. 14 is a graph showing the packaging of DNA by proheads.
Figure 15:
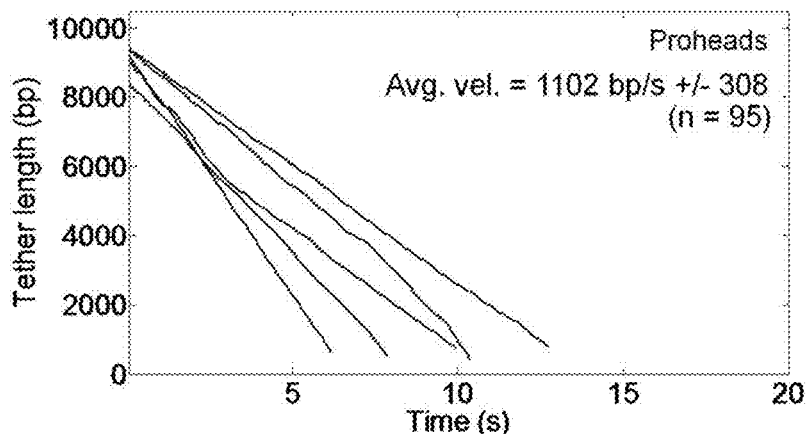
FIG. 15 is a graph showing the packaging of DNA by partial heads.
Figure 16:
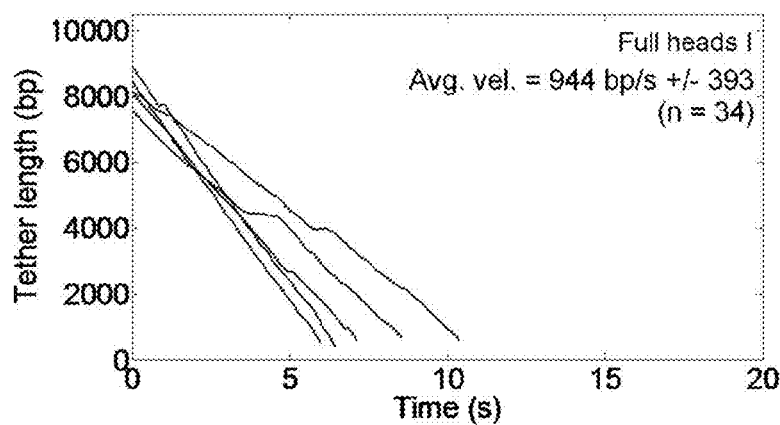
FIG. 16 is a graph showing the packaging of DNA by full heads.
Figure 17:
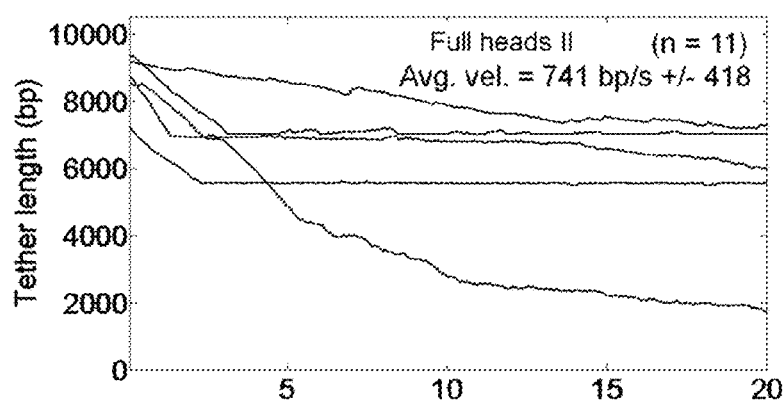
FIG. 17 is a graph showing the packaging of DNA by full heads.
Figure 18:
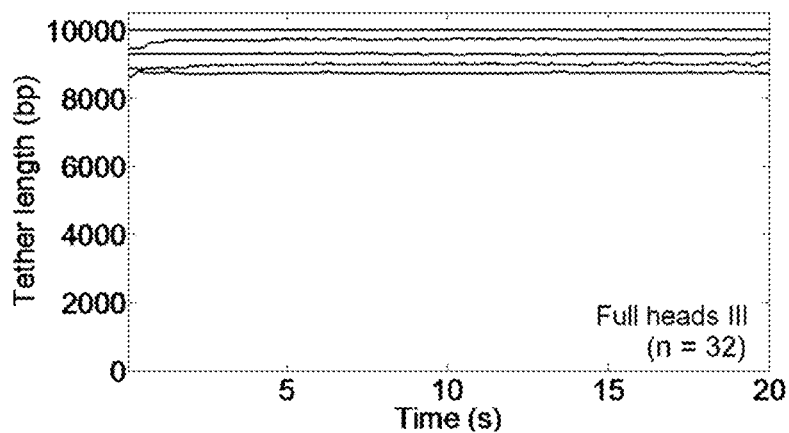
FIG. 18 is a graph showing the packaging of DNA by full heads.

The data shows that the packaging rates of the partial-head-assembled packaging machines (FIG. 14) are similar to those of the empty proheads (FIG. 16) (~800-1,100 bp/s). As described previously in Zheng et al., "A conformational switch in bacteriophage p22 portal protein primes genome injection," Mol Cell 29: 376-83 (2008), these rates are about seven times faster than those of the phi29 packaging machine. The full heads also packaged DNA but show distinctive features (FIGS. 16, 17 and 18). Some of the heads package the entire 10-kb DNA, and the packaging rates are similar to those of the partial-head- or prohead-assembled machines (FIG. 16). These heads presumably empty a significant portion of the packaged DNA during storage, creating room to accommodate a 10-kb piece. A second class of heads package only a short piece of DNA, about 1-3 kb, and then stall, suggesting that these heads may be nearly full and can only accommodate a small piece (FIG. 17). Interestingly, the packaging rates of these machines are still very high considering that these machines presumably packaged into a nearly full head. However, some of these machines did not stall completely but instead package slowly (e.g., the top and bottom traces in FIG. 17). A third class of heads simply form tethers, with no translocation evident, suggesting that these heads may have had no room left to accommodate additional DNA (FIG. 18). It is interesting that these machines form tethers, an indication that they successfully initiated packaging (as evident by a rise in force) but remain in the stalled state for a long period of time (otherwise, the DNA would rapidly slip out under 5 pN of force). These data demonstrate that the packaging machines can efficiently assemble on mature phage heads and refill the capsid, and that the length of refilled DNA appears to be dependent upon the amount of space available inside the capsid.

FIG. 13 shows the dual optical trap setup for single molecule DNA packaging. The T4 head-motor complex and the 10-kb DNA substrate are tethered between two beads, each held in an optical trap and held under 5 pN tension as described in Example 7 (FIGS. 14, 15, 16, 17 and 18). Packaging traces showing the packaging of DNA by proheads (FIG. 14), partial heads (FIG. 15), and full heads (FIGS. 16, 17 and 18). "n" represents the number of packaging traces qualitatively showing similar packaging behavior in that panel.

Example 4

Figure 25:
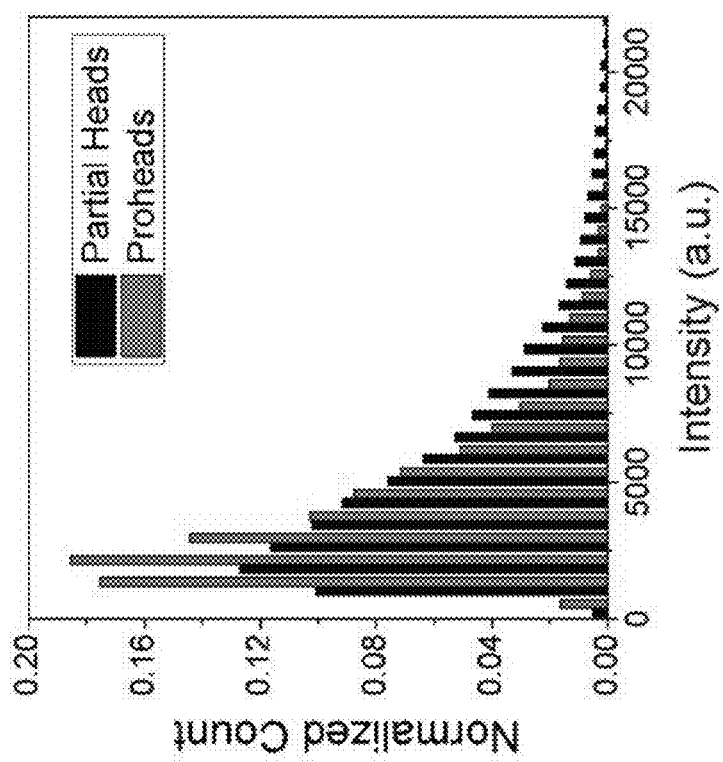
FIG. 25 is a normalized histogram showing single-head intensity for partial heads and proheads.
Figure 26:
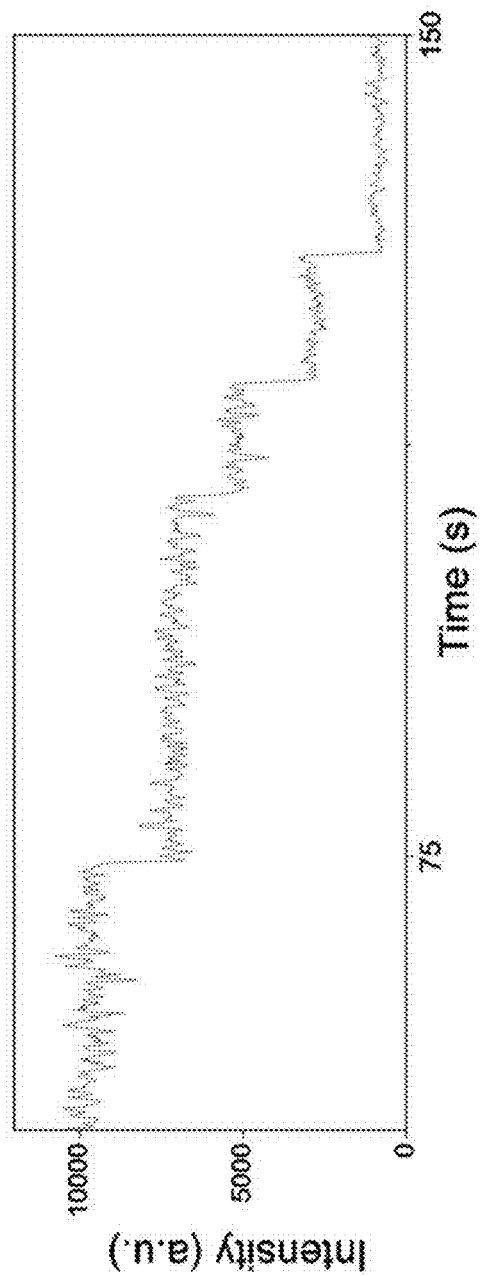
FIG. 26 is a graph showing the typical photobleaching steps from a single immobilized packaged head, packaged with multiple Cy5-labeled DNA fragments.

Mature-phage-head-assembled packaging machines undergo multiple packaging initiations. Short 39-bp Cy5-end-labeled and 83-bp Cy3-end-labeled DNAs are packaged into proheads, partial heads, and full heads using the bulk assay. The packaged heads are immobilized on polyethylene glycol (PEG)-passivated quartz surface using anti-phage-T4 polyclonal antibodies, and total internal reflection microscopy and single molecule detection are used to image the fluorescent particles. The "glowing" heads are quantified by determining the average number of bright spots per area from at least 30 images per sample (FIGS. 19 and 21; see FIGS. 23 and 24 for fluorescent images). Consistent with the bulk assays, the average number of bright spots corresponding to partial heads that package the labeled DNA is about 5-fold greater than for the empty proheads, and about 10-fold greater than for the full heads (FIGS. 20 and 22). Control experiments, which omitted gp17, had 0-2 bright spots, suggesting that nonspecific fluorescence of any surface-bound material is negligible (the packaged samples were treated with excess DNAse I [10 μg/ml] at room temperature for about 20 h to digest any unpackaged or nonspecifically bound DNA. Moreover, an analysis of the fluorescence intensity histograms of individual heads that package fluorescent DNA show that the weighted average intensity for individual head samples is around 5,500 units (arbitrary units), while the same for proheads was 4,000 units, suggesting that the partial head package more DNA molecules than the prohead (FIG. 25). This is further quantified by the number of photobleaching steps needed to bleach the fluorescent signal of each spot (FIG. 26). These data show that the partial heads contain on average five to six DNA molecules per head, whereas the proheads and full heads contain four DNA molecules per head. Thus, the mature phage heads, like the procapsids, can undergo multiple packaging initiations. The single molecule data also suggest that the large difference in packaging efficiency between the partial head, the full head, and the prohead arises from the inability to initiate packaging in a large fraction of full heads and proheads. For heads that are capable of initiating DNA packaging, the number of molecules packaged is only slightly different between the three species.

Figure 19:
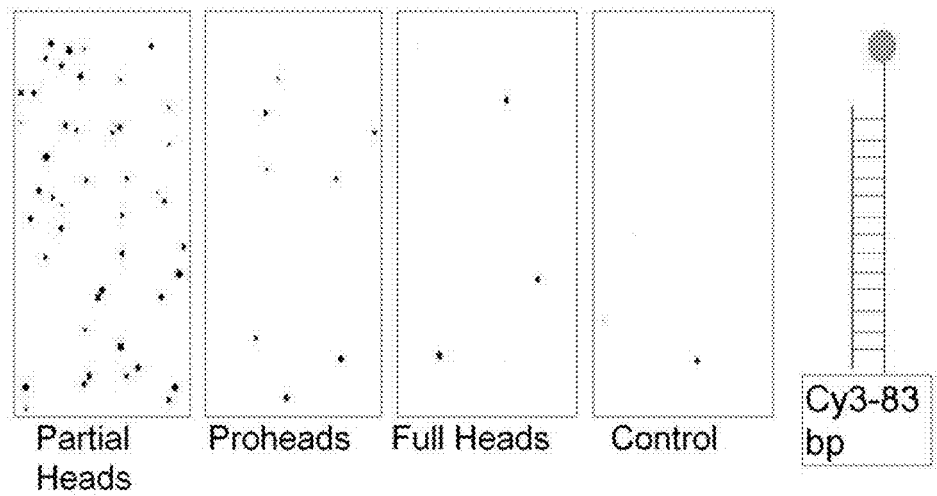
FIG. 19 is a schematic image showing the quantification of fluorescence images of immobilized T4 heads packaged with Cy3 DNA.
Figure 20:
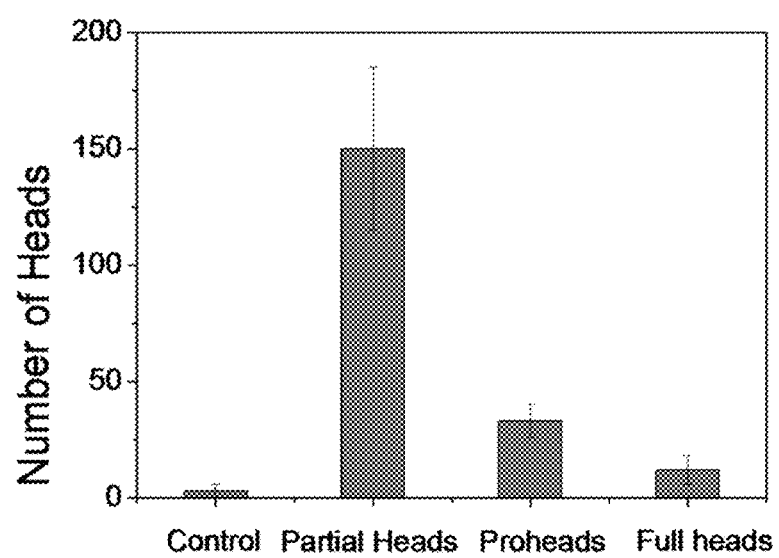
FIG. 20 is a schematic image showing the quantification of fluorescence images of immobilized T4 heads packaged with Cy5.
Figure 21:
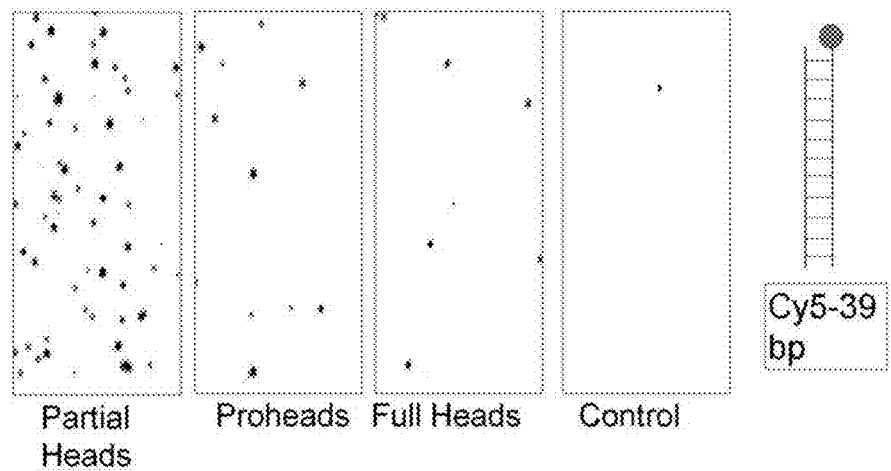
FIG. 21 is a histogram showing the number of heads packaged with Cy3 DNA in a single molecule fluorescence assay.
Figure 22:
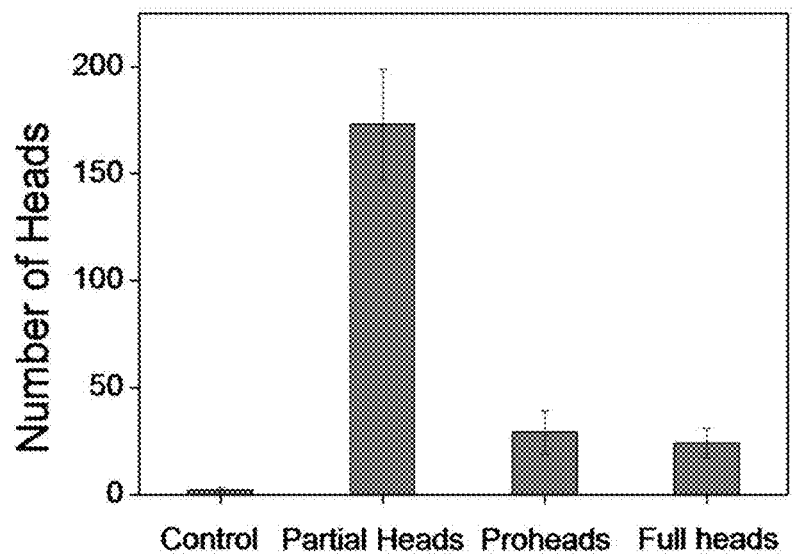
FIG. 22 is a histogram showing the number of heads packaged with Cy5 DNA in a single molecule fluorescence assay.

FIGS. 19, 20, 21 and 22 show quantification of packaging by single molecule fluorescence assay. FIGS. 19 and 21 show fluorescence images of immobilized T4 heads packaged with Cy3 (83-bp) and Cy5 (39-bp) DNAs, respectively. One-fourth of the 70 μm×35 lam imaging area is shown in each case (see FIGS. 23 and 24 for full-size fluorescent images). FIGS. 20 and 22 show histograms showing the number of heads packaged with Cy3 or Cy5 DNAs. The number of heads showing fluorescence in more than 30 images is averaged in each case.

Figure 23:
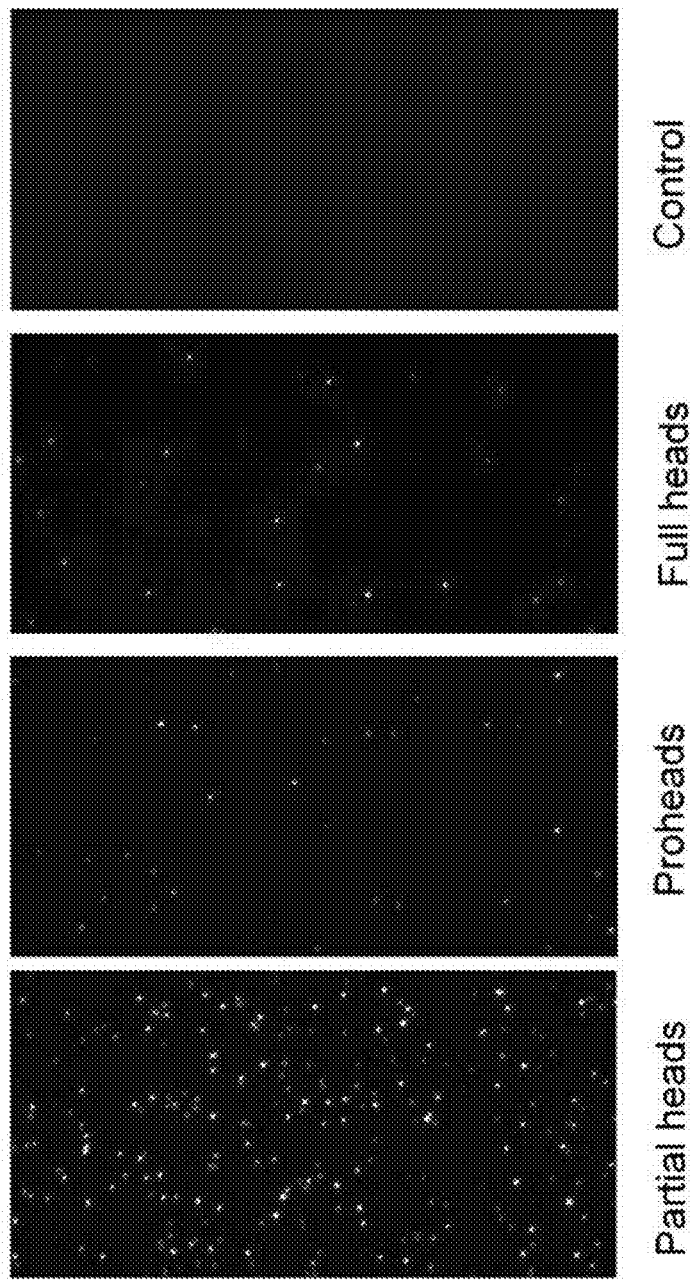
FIG. 23 shows representative images of partial heads, proheads, or full heads packaged with Cy5 39-bp DNA.

FIG. 23 shows Single molecule fluorescence of heads packaged with Cy5 39-bp DNA. Representative images of partial heads, proheads, or full heads packaged with Cy5 39-bp DNA. The imaging area is 70 μm×35 μm. Incubation time, laser intensity, imaging, and analysis parameters are the same for all samples.

Figure 24:
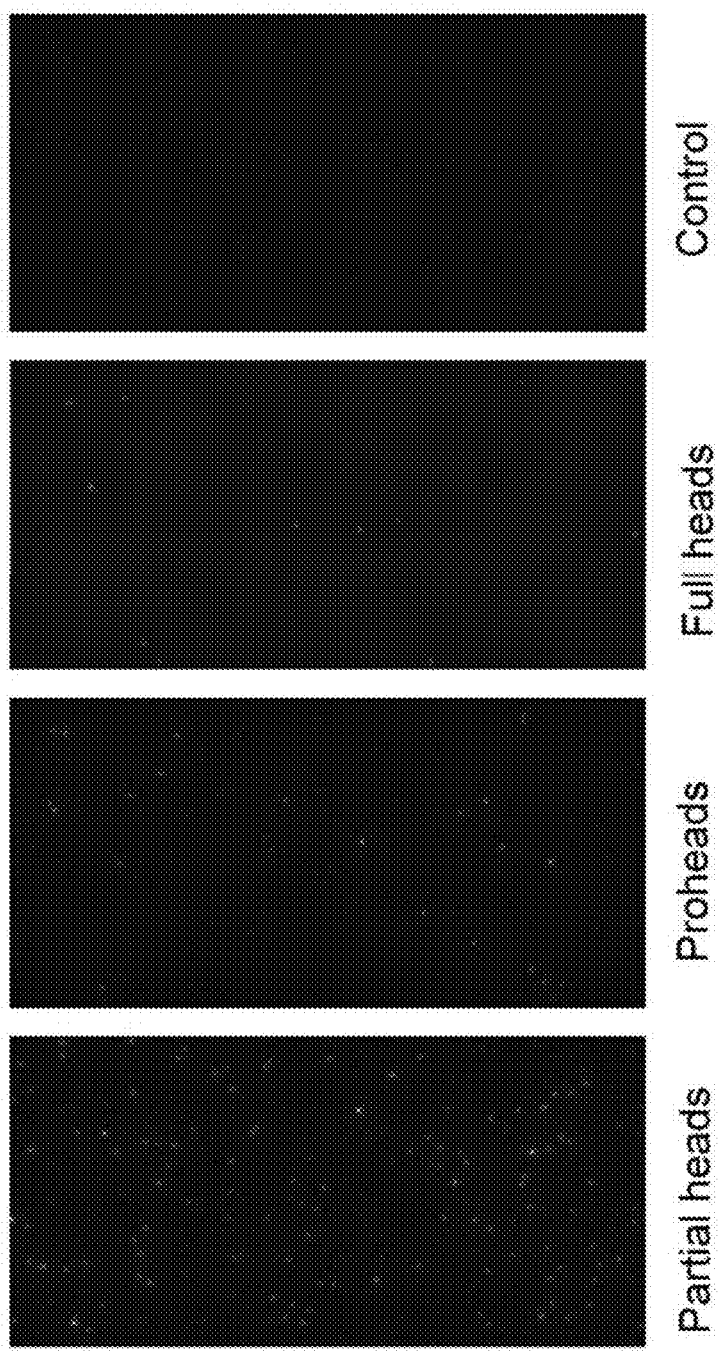
FIG. 24 shows representative images of partial heads, proheads, or full heads packaged with Cy3 83-bp DNA.

FIG. 24 shows Single molecule fluorescence of heads packaged with Cy3 83-bp DNA. Representative images of partial heads, proheads, and full heads packaged with Cy3 83-bp DNA. The imaging area is 70 μm×35 μm. Incubation time, laser intensity, imaging, and analysis parameters are the same for all samples.

FIG. 25 shows single head intensity for partial heads and proheads packaged with Cy3 83-bp DNA. Normalized histograms showing single head intensity for partial heads and proheads. Intensity from more than 2,000 fluorescent particles was analyzed in each case. The intensity of partial heads was brighter than that of proheads. About 46% of imaged partial heads and only about 29% of proheads have intensity above 5,000, suggesting that the partial heads package more oligonucleotide molecules than the proheads.

FIG. 26 shows Photobleaching of a single packaged head. Typical photobleaching steps from a single immobilized packaged head, packaged with multiple Cy5-labeled DNA fragments. Each step corresponds to one packaged labeled DNA.

Example 5

Purification of 10am13 am heads. The phage heads, both partial heads and full heads, are isolated from the *Escherichia coli* P301 infected with 10am13 am mutant. Proheads are isolated from the *E. coli* infected with 17am18amrII mutant. Proheads and phage heads are purified according to the procedures described above. Briefly, the infected cells (500-ml culture) are lysed in 40 ml of Pi—Mg buffer (26 mM Na2HPO4, 68 mM NaCl, 22 mM KH2PO4, 1 mM MgSO4 (pH 7.5) containing 10 μg/ml DNAse I and chloroform (1 ml) and incubated at 37° C. for 30 min to digest DNA. The lysate is centrifuged at 4,300 g for 10 min., and the supernatant is centrifuged at 34,500 g for 45 min. The supernatant is resuspended in 2.5 ml of 50 mM Tris-HCl (pH 7.5) and 5 mM MgCl2, and again subjected to low- and high-speed centrifugations. The head pellet is then resuspended in 200 μl of Tris-Mg buffer and purified by CsCl density gradient centrifugation. The head bands (FIG. 2) are extracted and dialyzed overnight against 10 mM Tris-HCl (pH 7.5), 50 mM NaCl, and 5 mM MgCl2. The two closely spaced bands at the top are pooled and further purified by DEAE-Sepharose chromatography (FIG. 3). The peak fractions are concentrated and stored at 4° C.

Example 6

Bulk in vitro DNA packaging. In vitro DNA packaging assays are performed by the procedure described above. The reaction mixture contains purified proheads, partial heads, or full heads (0.5–1×1010 particles), purified full-length gp17 (1.5 μM), and DNA (300 ng of 50- to 766-bp ladder DNA [New England Biolabs], 100 ng of Cy3 83-bp DNA, 50 ng of Cy5 39-bp DNA, or 600 ng of 48.5-kb phage λ DNA). The λ DNA is packaged using a buffer containing 30 mM Tris-HCl (pH 7.5), 100 mM NaCl, 3 mM MgCl2, and 1 mM ATP. The Cy3 and Cy5 DNAs are packaged using the 5% PEG buffer as described above. The packaging reactions are terminated by the addition of DNAse I, and the encapsidated DNAse I-resistant DNA is released by treatment with proteinase K and analyzed by agarose gel electrophoresis. Each experiment included one to several negative controls that lacked one of the essential packaging components: head, gp17, ATP, or DNA. Packaging efficiency is defined as the number of DNA molecules packaged per the number of head particles used in the packaging reaction.

Example 7

Single-molecule optical tweezers packaging. The packaging complexes are prepared by mixing purified heads (4×109 particles) with purified 1 μM full-length gp17 and 0.44 μM 125-bp dsDNA "priming" DNA (Z. Z. and V. B. R., unpublished data) in the presence of 1 mM ATP-γ-S in a 10-μl reaction volume consisting of packaging buffer (50 mM Tris-HCl [pH 7.6], 100 mM NaCl, and 5 mM MgCl2). The mixture is incubated at 37° C. for 30 min. The T4-phage-antibody-coated polystyrene beads (1.5 μl) (0.79 μm in diameter, Spherotech) are added to the above reaction mixture and incubated at 37° C. for 30 min.

The DNA beads are prepared by adding PCR-amplified 10-kb λ DNA biotinylated at one end to the streptavidin-coated polystyrene beads (0.86 μm in diameter, Spherotech) and incubated at 37° C. for 30 min. The dual-trap optical tweezers are set up and calibrated as described in Bustamante et al., "High resolution dual trap optical tweezers with differential detection," *Single-molecule techniques: a laboratory manual*, Selvin et al., editors, Woodbury, N.Y.: Cold Spring Harbor Laboratory Press. 297-324 (2007); and Chemla et al., "Mechanism of force generation of a viral DNA packaging motor," Cell 122: 683-692 (2005). Single molecule measurements are taken at 100 Hz in a "force-feedback" mode, where packaging is allowed to occur against a constant force of 5 pN. Tether formation and packaging is initiated by infusing packaging buffer containing 1 mM ATP into the flow cell. To prevent the formation of reactive singlet oxygen species, an oxygen scavenging system is used (100 μg/ml glucose oxidase, 20 μg/ml catalase, and 4 mg/ml glucose). The contour length of DNA is calculated from the measured force and extension between the beads using the worm-like chain model assuming a persistence length of 53 nm, a stretch modulus of 1,200 pN and a distance per basepair of 0.34 nm. The velocity of DNA packaging is determined from a linear fit of the contour length of DNA over a sliding window of 0.1 s (ten data points).

Example 8

Single Molecule Fluorescence of Packaged Heads. Single molecule fluorescence experiments to quantify packaging efficiency of different heads are performed on a wide field prism-type total internal reflection microscope with a 532 laser (Coherent) for Cy3 excitation or a 630 laser (Melles Griot) for Cy5 excitation. Immobilized capsids are imaged by a charged-coupled-device camera (iXon DV 887-BI; Andor Technology) at 100-ms time resolution. A homemade C++ program is used to record and analyze the images as described in Roy et al., "A practical guide to single-molecule FRET," *Nat. Methods* 5: 507-16 (2008).

To minimize nonspecific surface binding, clean quartz slides and glass cover slips are surface-passivated with PEG and 3% biotinylated PEG (Laysan Bio) [43]. After assembling the channel, NeutrAvidin (Thermo Scientific) is added (0.2 mg/ml), followed by incubation with biotinylated protein-G (Rockland Immunochemicals) (25 nM) for 30 min at room temperature. Subsequently, T4 phage antibody (15 nM) is added and incubated for 1 h. The packaged heads with 83-bp Cy3 and 39-bp Cy5 DNAs are applied to separate channels and incubated for 20 min. The packaging reaction mixtures are treated with DNAse I (10 μg/ml) at room temperature for about 20 h to digest any unpackaged or nonspecifically bound Cy3 and Cy5 DNAs. The unbound packaged heads are washed off, and immobilized capsids are imaged in 50 mM Tris-Cl buffer (pH 8), 5% PEG, 5 mM MgCl2, 1 mM spermidine, 1 mM putrescene, 60 mM NaCl, and an oxygen scavenger system (0.8% dextrose, 0.1 mg/ml glucose oxidase, 0.02 mg/ml catalase, and 3 mM Trolox) as further described in Rasnik et al., "Branch migration enzyme as a Brownian ratchet," *EMBO J.* 27: 1727-35 (2008).

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising:
   attaching a packaging motor to a carrier, and
   packaging an exogenous nucleic acid into the carrier to thereby form a packaging machine,
   wherein the carrier comprises a mature capsid of a bacteriophage, and wherein the mature capsid is neck-less.
2. The method according to claim 1, wherein the carrier comprises a mature capsid of a bacteriophage T4.
3. The method according to claim 1, wherein the exogenous nucleic acid is DNA.
4. The method according to claim 3, wherein the DNA is double stranded.
5. The method according to claim 1, wherein the carrier comprises a liposomal vesicle.
6. The method according to claim 5, wherein the packaging motor comprises a protein complex.
7. The method according to claim 6, wherein the protein complex comprises ATPase activity.
8. The method according to claim 7, wherein the protein complex comprises a gp17 protein.
9. The method according to claim 8, wherein the exogenous nucleic acid is DNA.
10. The method according to claim 9, wherein the DNA is double stranded.
11. The method according to claim 1, wherein the carrier comprises a peptide-like component displayed on a surface of the mature capsid of the virus.
12. The method according to claim 11, wherein the peptide-like component is a polypeptide or fragment thereof.
13. The method according to claim 12, wherein the polypeptide or fragment thereof is immunogenic.
14. The method according to claim 13, wherein the polypeptide or fragment thereof is an antigen.
15. The method according to claim 1, wherein the attaching and packaging processes are conducted in vitro.
16. The method according to claim 1, wherein the packaging motor comprises a protein complex with an ATPase activity.
17. The method according to claim 16, wherein the protein complex comprises a gp17 protein.
18. The method according to claim 1, wherein the mature capsid is full of bacteriophage genome DNA.
19. The method according to claim 1, wherein the mature capsid contains a small portion of bacteriophage genome DNA.
20. The method according to claim 1, wherein the mature capsid is isolated from a bacterial cell infected with a bacteriophage genome comprising a mutation in a gene coding for a neck protein, and wherein the mutation causes forming a mature capsid that is neck-less in the bacterial cell.
21. The method according to claim 20, wherein the bacteriophage genome comprises mutations in a gene coding for a tail protein and in a gene coding for a neck protein, wherein the mutations cause forming a mature capsid that is neck-less and tail-less in the bacterial cell, and wherein the mature capsid that is isolated from the bacterial cell is neck-less and tail-less.
22. The method according to claim 2, wherein the mature capsid of the bacteriophage T4 is neck-less.
23. The method according to claim 22, wherein the mature capsid is isolated from a bacterial cell infected with a bacteriophage T4 genome comprising a mutation in gene 13, and wherein the mutation in gene 13 causes forming a mature capsid of bacteriophage T4 that is neck-less in the bacterial cell.
24. The method according to claim 23, wherein the bacteriophage T4 genome comprises mutations in gene 10 and gene 13, wherein the mutations in gene 10 and gene 13 cause forming a mature capsid that is neck-less and tail-less in the bacterial cell, and wherein the mature capsid that is isolated from the bacterial cell is neck-less and tail-less.

* * * * *